United States Patent [19]
Campbell et al.

[11] Patent Number: 4,889,545
[45] Date of Patent: Dec. 26, 1989

[54] HYDROCARBON GAS PROCESSING

[75] Inventors: Roy E. Campbell; John D. Wilkinson; Hank M. Hudson, all of Midland, Tex.

[73] Assignee: Elcor Corporation, Midland, Tex.

[21] Appl. No.: 275,102

[22] Filed: Nov. 21, 1988

[51] Int. Cl.[4] .............................................. F25J 3/02
[52] U.S. Cl. .......................................... 62/24; 62/39; 62/43
[58] Field of Search .................... 62/11, 23, 24, 38, 39, 62/43

[56] References Cited

U.S. PATENT DOCUMENTS

| | | | |
|---|---|---|---|
| 3,516,261 | 6/1970 | Hoffman | 62/24 |
| 3,656,311 | 4/1972 | Kaiser | 62/28 |
| 3,902,329 | 9/1975 | King, III et al. | 62/17 |
| 4,002,042 | 1/1977 | Pryor et al. | 62/28 |
| 4,004,430 | 1/1977 | Solomon et al. | 62/18 |
| 4,115,086 | 9/1978 | Jordan et al. | 62/28 |
| 4,132,604 | 1/1979 | Alexion et al. | 203/87 |
| 4,157,904 | 6/1979 | Campbell et al. | 62/27 |
| 4,171,964 | 10/1979 | Campbell et al. | 62/24 |
| 4,203,741 | 5/1980 | Bellinger et al. | 62/24 |
| 4,251,249 | 2/1981 | Gulsby | 62/28 |
| 4,278,457 | 7/1981 | Campbell et al. | 62/24 |
| 4,356,014 | 10/1982 | Higgins | 62/24 |
| 4,507,133 | 3/1985 | Khan et al. | 62/29 |
| 4,592,766 | 6/1986 | Kumman et al. | 62/18 |
| 4,596,588 | 6/1986 | Cook | 62/26 |
| 4,617,039 | 10/1986 | Buck | 62/26 |
| 4,657,571 | 4/1987 | Gazzi | 62/17 |
| 4,687,499 | 8/1987 | Aghili | 62/24 |
| 4,711,651 | 12/1987 | Sharma et al. | 62/24 |
| 4,738,699 | 4/1988 | Apffel et al. | 62/24 |
| 4,746,342 | 5/1988 | DeLong et al. | 62/24 |

Primary Examiner—Ronald C. Capossela
Attorney, Agent, or Firm—Brumbaugh, Graves, Donohue & Raymond

[57] ABSTRACT

A process for the recovery of ethane, ethylene, propane, propylene and heavier hydrocarbon components from a hydrocarbon gas stream is disclosed. The stream is divided into first and second streams. The first stream is cooled to condense substantially all of it and is thereafter expanded to the fractionation tower pressure. After expansion, the cooled first stream is directed in heat exchange relation with a compressed recycle portion of the fractionation tower overhead. The warmed first stream is then supplied to the fractionation tower at a first mid-column feed position. The second stream is expanded to the tower pressure and is then supplied to the column at a second mid-column feed position. The recycle stream is cooled by the first stream sufficiently to substantially condense it. The substantially condensed recycle stream is then expanded to the pressure of the distillation column and supplied to the column at a top column feed position. The pressure of the recycle stream and the quantities and temperatures of the feeds to the column are effective to maintain the column overhead temperature at a temperature whereby the major portion of the desired components is recovered.

72 Claims, 10 Drawing Sheets

HYDROCARBON GAS PROCESSING

BACKGROUND OF THE INVENTION

This invention relates to a process for the separation of a gas containing hydrocarbons.

Ethylene, ethane, propylene, propane and heavier hydrocarbons can be recovered from a variety of gases, such as natural gas, refinery gas, and synthetic gas streams obtained from other hydrocarbon materials such as coal, crude oil, naphtha, oil shale, tar sands, and lignite. Natural gas usually has a major proportion of methane and ethane, i.e. methane and ethane together comprise at least 50 mole percent of the gas. The gas may also contain relatively lesser amounts of heavier hydrocarbons such as propane, butanes, pentanes, and the like as well as hydrogen, nitrogen, carbon dioxide and other gases.

The present invention is generally concerned with the recovery of ethylene, ethane, propylene, propane and heavier hydrocarbons from such gas streams. A typical analysis of a gas stream to be processed in accordance with this invention would be, in approximate mole percent, 92.5% methane, 4.2% ethane and other $C_2$ components, 1.3% propane and other $C_3$ components, 0.4% iso-butane, 0.3% normal butane, 0.5% pentanes plus, with the balance made up of nitrogen and carbon dioxide. Sulfur containing gases are also sometimes present.

Recent fluctuations in the prices of both natural gas and its NGL constituents have reduced the incremental value of ethane and heavier components as liquid products. This has resulted in a demand for processes which can provide more efficient recoveries of these products. Available processes for separating these materials include those based upon cooling and refrigeration of the gas, oil absorption, and refrigerated oil absorption. Additionally, cryogenic processes have become popular because of the availability of economical equipment which produces power while simultaneously expanding and extracting heat from the gas being processed. Depending upon the pressure of the gas source, the richness (ethane and heavier hydrocarbons content) of the gas, and the desired end products, each of these processes or a combination thereof may be employed.

The cryogenic expansion process is now generally preferred for ethane recovery because it provides maximum simplicity with ease of start up, operating flexibility, good efficiency, safety, and good reliability. U.S. Pat. Nos. 4,157,904, 4,171,964, and 4,278,457 and our pending U.S. patent applications, Ser. Nos. 194,822 and 194,878, both filed on May 17, 1988, describe relevant processes.

In a typical cryogenic expansion recovery process, a feed gas stream under pressure is cooled by heat exchange with other streams of the process and/or external sources of refrigeration such as a propane compression-refrigeration system. As the gas is cooled, liquids may be condensed and collected in one or more separators as high-pressure liquids containing some of the desired $C_2+$ components. Depending on the richness of the gas and the amount of liquid formed, the high-pressure liquids may be expanded to a lower pressure and fractionated. The vaporization occurring during expansion of the liquid results in further cooling of the stream. Under some conditions, pre-cooling the high pressure liquid prior to the expansion may be desirable in order to further lower the temperature resulting from the expansion. The expanded stream, comprising a mixture of liquid and vapor, is fractionated in a distillation (demethanizer) column. In the column, the expansion-cooled stream(s) is (are) distilled to separate residual methane, nitrogen, and other volatile gases as overhead vapor from the desired $C_2$ components, $C_3$ components, and heavier components as bottom liquid product.

If the feed gas is not totally condensed (typically it is not), the vapor remaining from the partial condensation can be split into two or more streams. One portion of the vapor is passed through a work expansion machine or engine, or expansion valve, to a lower pressure at which additional liquids are condensed as a result of further cooling of the stream. The pressure after expansion is essentially the same as the pressure at which the fractionation column is operated. The combined vapor-liquid phases resulting from expansion are supplied as feed to the column.

The remaining portion of the vapor is cooled to substantial condensation by heat exchange with other process streams, e.g. the cold fractionation tower overhead. Depending on the amount of high-pressure liquid available, some or all of the high-pressure liquid may be combined with this vapor portion prior to cooling. The resulting cooled stream is then expanded through an appropriate expansion device, such as an expansion valve, to the pressure at which the demethanizer is operated. During expansion, a portion of the liquid will vaporize, resulting in cooling of the total stream. The flash expanded stream is then supplied as top feed to the demethanizer. Typically, the vapor portion of the expanded stream and the demethanizer overhead vapor combine in an upper, separator section in the fractionation tower as residual methane product gas. Alternatively, the cooled and expanded stream may be supplied to a separator to provide vapor and liquid streams. The vapor is combined with the tower overhead and the liquid is supplied to the column as a top column feed.

In the ideal operation of such a separation process, the residue gas leaving the process will contain substantially all of the methane in the feed gas with essentially none of the heavier hydrocarbon components and the bottoms fraction leaving the demethanizer will contain substantially all of the heavier components with essentially no methane or lighter components. In practice, however, this ideal situation is not obtained for the reason that the conventional demethanizer is operated largely as a stripping column. The methane product of the process, therefore, typically comprises vapors leaving the top fractionation stage of the column, together with vapors not subjected to any rectification step. Considerable losses of $C_2$ components occur because the top liquid feed contains substantial quantities of $C_2$ components and heavier components, resulting in corresponding equilibrium quantities of $C_2$ components and heavier components in the vapors leaving the top fractionation stage of the demethanizer. The loss of these desirable components could be significantly reduced if the rising vapors could be brought into contact with a significant quantity of liquid (reflux), containing very little $C_2$ components and heavier components; that is, reflux capable of absorbing the $C_2$ components and heavier components from the vapors. The present invention provides the means for achieving this objective and significantly improving the recovery of the desired products.

In accordance with the present invention, it has been found that $C_2$ recoveries in excess of 99 percent can be obtained. Similarly, in those instances when recovery of $C_2$ components is not desired, $C_3$ recoveries in excess of 99% can be achieved. In addition, the present invention makes possible essentially 100 percent separation of methane (or $C_2$ components) and lighter components from the $C_2$ components (or $C_3$ components) and heavier components at reduced energy requirements. The present invention, although applicable at lower pressures and warmer temperatures, is particularly advantageous when processing feed gases in the range of 600 to 1000 psia or higher under conditions requiring column overhead temperatures of $-110°$ F. or colder.

For a better understanding of the present invention, reference is made to the following examples and drawings. Referring to the drawings:

FIG. 1 is a flow diagram of a cryogenic expansion natural gas processing plant of the prior art according to U.S. Pat. No. 4,157,904;

FIG. 2 is a flow diagram of a cryogenic expansion natural gas processing plant of an alternative prior art process according to U.S. Pat. No. 4,687,499;

In the following explanation of the above figures, tables are provided summarizing flow rates calculated for representative process conditions. In the tables appearing herein, the values for flow rates (in pound moles per hour) have been rounded to the nearest whole number for convenience. The total stream rates shown in the tables include all nonhydrocarbon components and hence are generally larger than the sum of the stream flow rates for the hydrocarbon components. Temperatures indicated are approximate values, rounded to the nearest degree. It should also be noted that the process design calculations performed for the purpose of comparing the processes depicted in the figures are based on the assumption of no heat leak from (or to) the surroundings to (or from) the process. The quality of commercially available insulating materials makes this a very reasonable assumption and one that is typically made by those skilled in the art.

DESCRIPTION OF THE PRIOR ART

Figure 1:
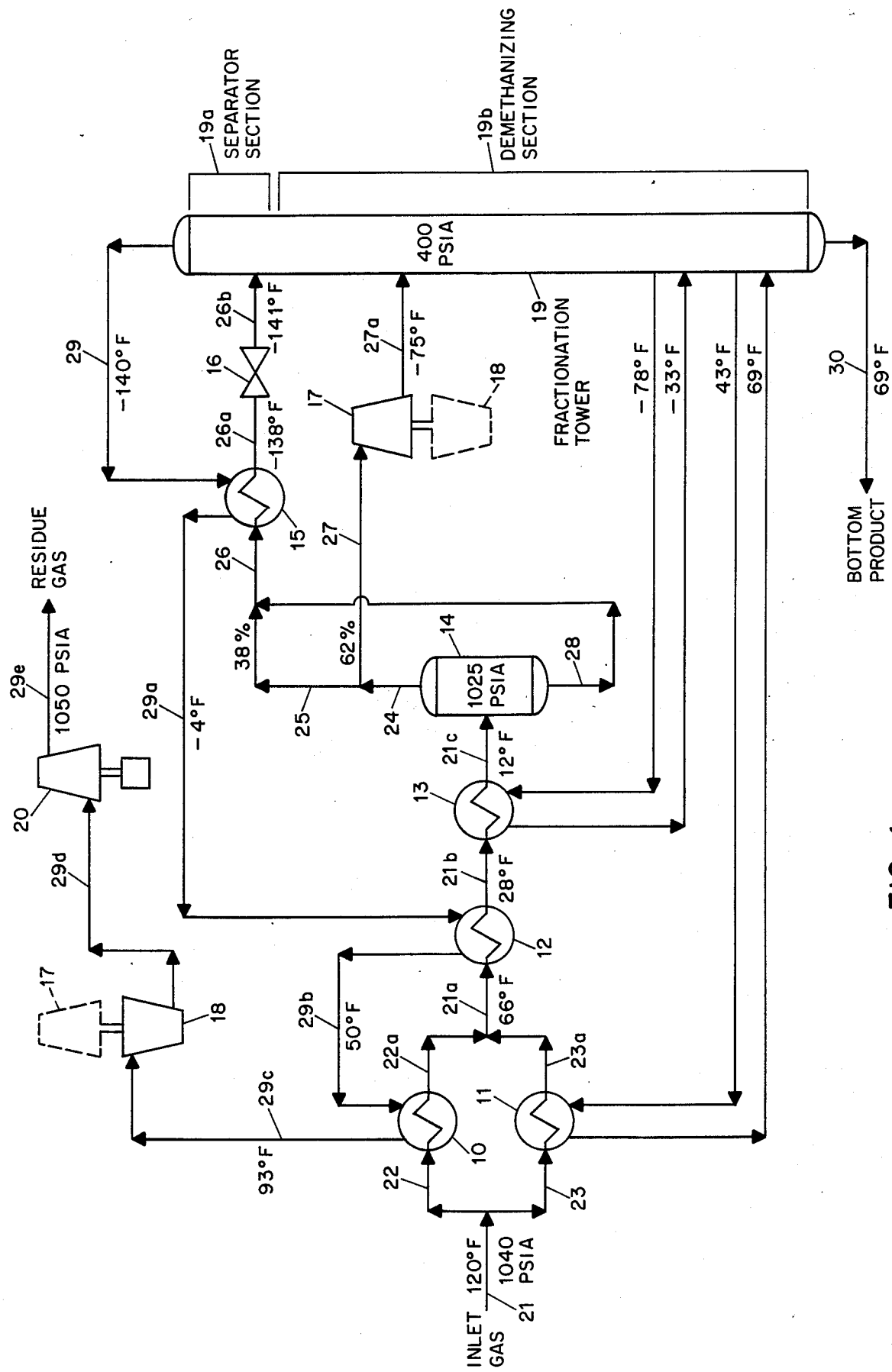

Referring now to FIG. 1, in a simulation of the process according to U.S. Pat. No. 4,157,904, inlet gas enters the plant at 120° F. and 1040 psia as stream 21. If the inlet gas contains a concentration of sulfur compounds which would prevent the product streams from meeting specifications, the sulfur compounds are removed by appropriate pretreatment of the feed gas (not illustrated). In addition, the feed stream is usually dehydrated to prevent hydrate (ice) formation under cryogenic conditions. Solid desiccant has typically been used for this purpose. The feed stream is divided into two parallel streams, 22 and 23, and cooled to 66° F. by heat exchange with cool residue gas at 50° F. in exchanger 10 and with demethanizer liquid at 43° F. in demethanizer reboiler 11. From these exchangers, streams 22a and 23a recombine as stream 21a which enters exchanger 12 where it is cooled to 28° F. (stream 21b) by cool residue gas at $-4°$ F. (stream 29a). The feed gas continues to demethanizer side reboiler 13 and is further cooled by heat exchange with demethanizer liquid at $-78°$ F. The further cooled stream 21c then enters separator 14 at 12° F. and 1025 psia where the vapor (stream 24) is separated from the condensed liquid (stream 28).

The vapor (stream 24) from separator 14 is divided into two streams, 25 and 27. Stream 25, containing about 38 percent of the total vapor, is combined with the separator liquid (stream 28). The combined stream 26 then passes through heat exchanger 15 in heat exchange relation with the demethanizer overhead vapor stream 29 resulting in cooling and substantial condensation of the combined stream. The substantially condensed stream 26a at $-138°$ F. is then flash expanded through an appropriate expansion device, such as expansion valve 16, to the operating pressure (approximately 400 psia) of the fractionation tower 19. During expansion a portion of the stream is vaporized, resulting in cooling of the total stream. In the process illustrated in FIG. 1, the expanded stream 26b leaving expansion valve 16 reaches a temperature of $-141°$ F, and is supplied to separator section 19a in the upper region of fractionation tower 19. The liquids separated therein become the top feed to demethanizing section 19b.

The remaining 62 percent of the vapor from separator 14 (stream 27) enters a work expansion machine 17 in which mechanical energy is extracted from this portion of the high pressure feed. The machine 17 expands the vapor substantially isentropically from a pressure of about 1025 psia to a pressure of about 400 psia, with the work expansion cooling the expanded stream 27a to a temperature of approximately $-75°$ F. The typical commercially available expanders are capable of recovering on the order of 80–85% of the work theoretically available in an ideal isentropic expansion. The expanded and partially condensed stream 27a is supplied as feed to the distillation column at an intermediate point.

The demethanizer in fractionation tower 19 is a conventional distillation column containing a plurality of vertically spaced trays, one or more packed beds, or some combination of trays and packing. As is often the case in natural gas processing plants, the fractionation tower may consist of two sections. The upper section 19a is a separator wherein the partially vaporized top feed is divided into its respective vapor and liquid portions, and wherein the vapor rising from the lower distillation or demethanizing section is combined with the vapor portion of the top feed to form the cold residue gas distillation stream 29 which exits the top of the tower. The lower, demethanizing section 19b contains the trays and/or packing and provides the necessary contact between the liquids falling downward and the vapors rising upward. The demethanizing section also includes reboilers which heat and vaporize a portion of the liquids flowing down the column to provide the stripping vapors which flow up the column. The bottom product stream 30 exits the bottom of the tower at 69° F., based on a typical specification of a methane to ethane ratio of 0.025:1 on a molar basis in the bottom product.

The residue gas (stream 29) passes countercurrently to the incoming feed gas in: (a) heat exchanger 15 where it is heated to −4° F. (stream 29a), (b) heat exchanger 12 where it is heated to 50° F. (stream 29b), and (c) heat exchanger 10 where it is heated to 93° F. (stream 29c). The residue gas is then re-compressed in two stages. The first stage is compressor 18 driven by the expansion machine 17. The second stage is compressor 20 driven by a supplemental power source which compresses the residue gas to 1050 psia (stream 29e), sufficient to meet line requirements (usually on the order of the inlet pressure).

A summary of stream flow rates and energy consumption for the process illustrated in FIG. 1 is set forth in the following table:

TABLE I (FIG. 1)
Stream Flow Summary - (Lb. Moles/Hr)

| Stream | Methane | Ethane | Propane | Butanes+ | Total |
|---|---|---|---|---|---|
| 21 | 25381 | 1161 | 362 | 332 | 27448 |
| 24 | 25323 | 1149 | 352 | 264 | 27298 |
| 28 | 58 | 12 | 10 | 68 | 150 |
| 25 | 9752 | 443 | 136 | 102 | 10513 |
| 27 | 15571 | 706 | 216 | 162 | 16785 |
| 29 | 25355 | 118 | 7 | 1 | 25607 |
| 30 | 26 | 1043 | 355 | 331 | 1841 |

| Recoveries* | |
|---|---|
| Ethane | 89.80% |
| Propane | 98.16% |
| Butanes+ | 99.53% |
| Horsepower | |
| Residue Compression | 13,061 |

*(Based on unrounded flow rates)

The prior art illustrated in FIG. 1 is limited to the ethane recovery shown in Table I by the equilibrium at the top of the column with the top feed to the demethanizer. Lowering the feed gas temperature at separator 14 below that shown in FIG. 1 will not increase the recovery appreciably, but will only reduce the power recovered in the expansion machine 17 and increase the residue compression horsepower correspondingly. The only way to significantly improve the ethane recovery of the prior art process of FIG. 1 is to lower the operating pressure of the demethanizer, but to do so will increase the residue compression horsepower inordinately. Even so, the ultimate ethane recovery possible will still be dictated by the composition of the top liquid feed to the demethanizer.

Figure 2:
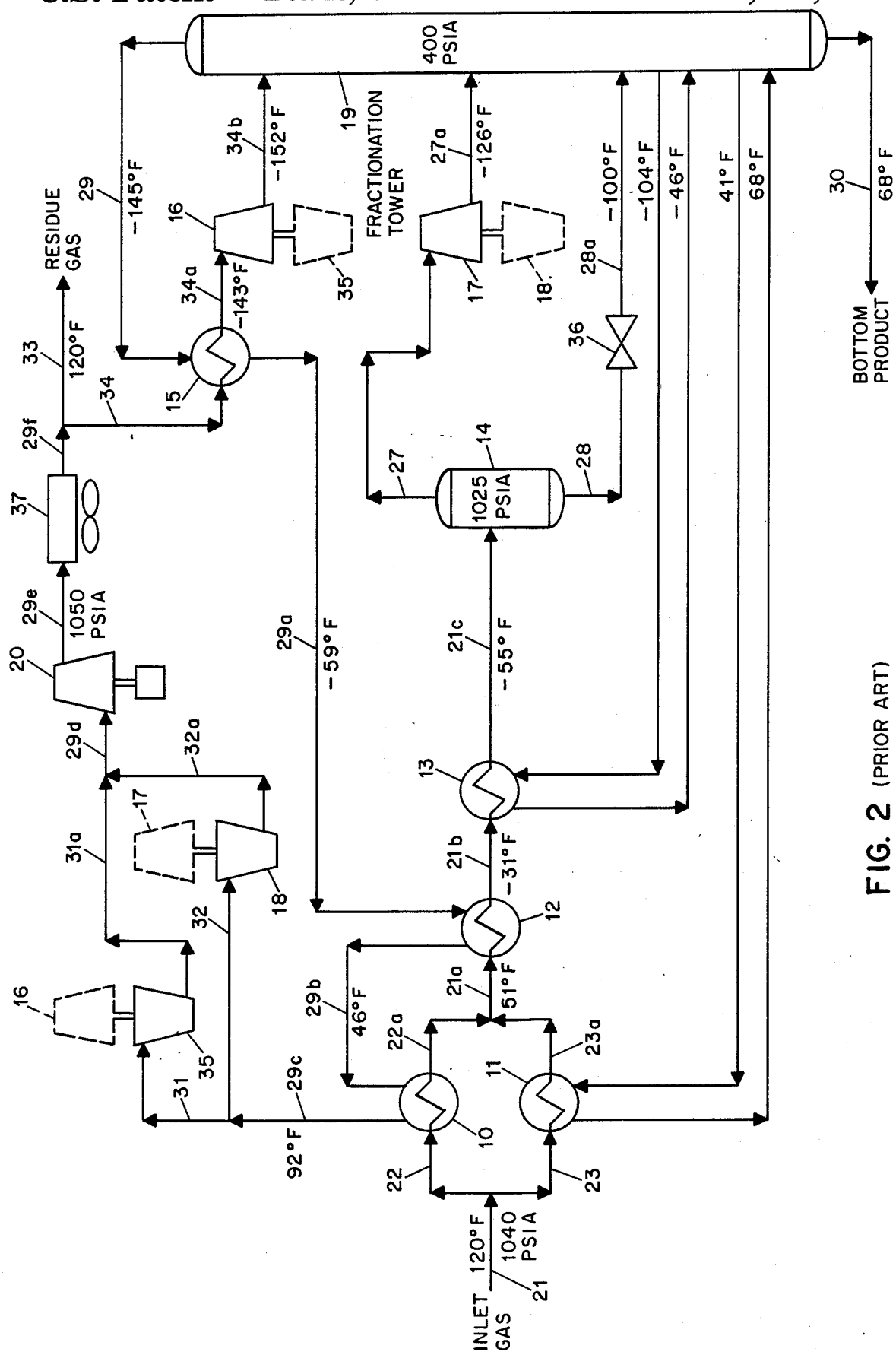

One way to achieve higher ethane recovery with the same demethanizer operating pressure is to create a leaner (lower $C_2+$ content) top feed. FIG. 2 represents an alternative prior art process in accordance with U.S. Pat. No. 4,687,499 that recycles a portion of the residue gas product to provide a leaner top feed to the demethanizer. The process of FIG. 2 is based on the same feed gas composition and conditions as described above for FIG. 1. In the simulation of this process, as in the simulation for the process of FIG. 1, operating conditions were selected to minimize energy consumption for a given recovery level. The feed stream 21 is divided into two parallel streams, 22 and 23, and cooled to 51° F. by heat exchange with cool residue gas at 46° F. in exchanger 10 and demethanizer liquid at 41° F. in demethanizer reboiler 11. From these exchangers, streams 22a and 23a recombine and stream 21a enters exchanger 12 where it is further cooled to −31° F. (stream 21b) by cool residue gas at −59° F. (stream 29a). The feed gas continues to demethanizer side reboiler 13 and is cooled by heat exchange with demethanizer liquid at −104° F. The feed stream 21c then enters separator 14 at −55° F. and a pressure of 1025 psia where the vapor (stream 27) is separated from the condensed liquid (stream 28).

The vapor from separator 14 (stream 27) enters a work expansion machine 17 in which mechanical energy is extracted from this portion of the high pressure feed. The machine 17 expands the vapor substantially isentropically from a pressure of about 1025 psia to the operating pressure of the demethanizer of about 400 psia, with the work expansion cooling the expanded stream to a temperature of approximately −126° F. The expanded and partially condensed stream 27a is supplied as feed to the distillation column at an intermediate point. The separator liquid (stream 28) is likewise expanded to 400 psia by expansion valve 36, cooling stream 28 to −100° F. (stream 28a) before it is supplied to the demethanizer in fractionation tower 19 at a lower mid-column feed point.

A portion of the high pressure residue gas (stream 34) is withdrawn from the main residue flow (stream 29f) to become the top distillation column feed. Recycle gas stream 34 passes through heat exchanger 15 in heat exchange relation with the cold demethanizer overhead distillation vapor stream 29 resulting in cooling and substantial condensation of the recycle stream. The cooled stream 34a at −143° F. is then expanded through an appropriate expansion device, such as expansion machine 16. The machine 16 expands the stream substantially isentropically from a pressure of about 1040 psia to the demethanizer operating pressure of about 400 psia, with the work expansion cooling the expanded stream to a temperature of approximately −152° F. (stream 34b). The expanded stream 34b is supplied to the tower as the top feed.

The bottom liquid product stream 30 exits the bottom of tower 19 at 68° F. The cold residue gas (stream 29) at a temperature of −145° F. passes countercurrently to the recycle gas stream in heat exchanger 15 where it is heated to −59° F. (stream 29a). The residue gas then passes countercurrently to the incoming feed gas in heat exchanger 10 where it is heated to 46° F. (stream 29b) and in heat exchanger 10 where it is heated to 92° F. (stream 29c). The residue gas is then re-compressed in two stages. Stream 29c is split into parallel streams 31 and 32 which flow to compressors 35 and 18 (driven by the expansion machines 16 and 17 respectively) for the first stage of compression. Streams 31a and 32a recombine and stream 29d flows to the second stage of compression (compressor 20 driven by a supplemental power source) which compresses the residue gas to the line pressure of 1050 psia (stream 29e). After stream 29e is cooled to 120° F. (stream 29f) by heat exchanger 37, the recycle stream 34 is withdrawn and the residue gas product (stream 33) flows to the sales pipeline.

A summary of stream flow rates and energy consumption for the process illustrated in FIG. 2 is set forth in the following table:

TABLE II (FIG. 2)
Stream Flow Summary - (lb. Moles/Hr)

| Stream | Methane | Ethane | Propane | Butanes+ | Total |
|---|---|---|---|---|---|
| 21 | 25381 | 1161 | 362 | 332 | 27448 |
| 27 | 24685 | 1050 | 285 | 158 | 26380 |
| 28 | 696 | 111 | 77 | 174 | 1068 |

TABLE II-continued (FIG. 2)
Stream Flow Summary - (lb. Moles/Hr)

| 34 | 7259 | 3 | 0 | 0 | 7300 |
|---|---|---|---|---|---|
| 29 | 32611 | 15 | 0 | 0 | 32795 |
| 30 | 29 | 1149 | 362 | 332 | 1953 |
| 33 | 25352 | 12 | 0 | 0 | 25495 |

| Recoveries* | |
|---|---|
| Ethane | 98.99% |
| Propane | 100.00% |
| Butanes+ | 100.00% |
| Horsepower | |
| Residue Compression | 17,380 |

*(Based on un-rounded flow rates)

DESCRIPTION OF THE INVENTION

Example 1

Figure 3:
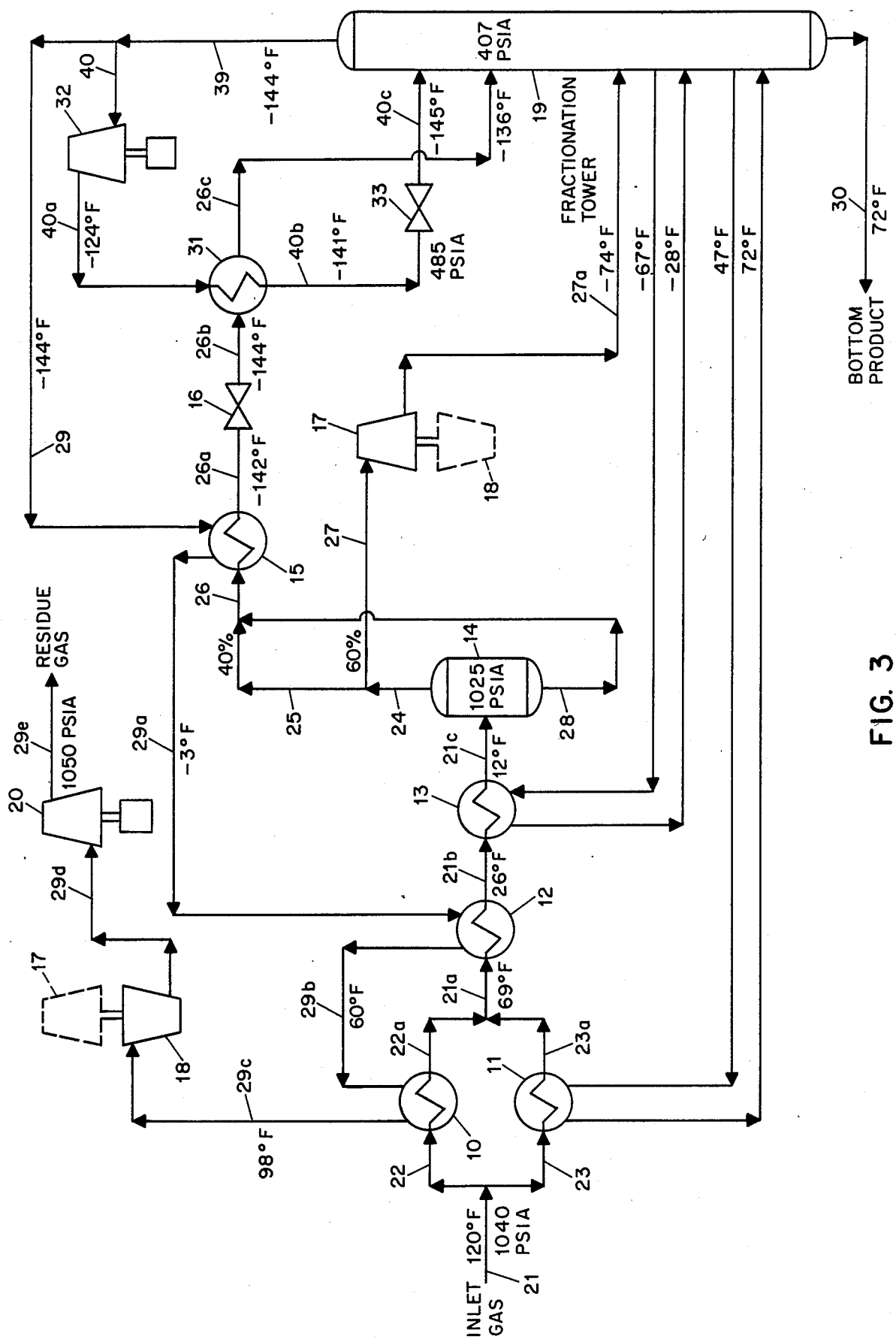
FIG. 3 is a flow diagram of a natural gas processing plant in accordance with the present invention.

FIG. 3 illustrates a flow diagram of a process in accordance with the present invention. The feed gas composition and conditions considered in the process illustrated in FIG. 3 are the same as those in FIGS. 1 and 2. Accordingly, the FIG. 3 process can be compared with the FIGS. 1 and 2 processes to illustrate the advantages of the present invention.

In the simulation of the FIG. 3 process, inlet gas enters at 120° F. and a pressure of 1040 psia as stream 21. The feed stream is divided into two parallel streams, 22 and 23, and cooled to 69° F. by heat exchange with cool residue gas at 60° F. (stream 29b) in exchanger 10 and with demethanize liquid at 47° F. in demethanizer reboiler 11. From these exchangers, streams 22a and 23a recombine and stream 21a enters exchanger 12 where it is cooled to 26° F. (stream 21b) by cool residue gas at −3° F. (stream 29a). The further cooled stream 21b continues to demethanizer side reboiler 13 and is cooled by heat exchange with demethanizer liquid at −67° F. The feed stream 21c then enters high pressure separator 14 at 12° F. and a pressure of 1025 psia where the vapor (stream 24) is separated from condensed liquid (stream 28).

The vapor (stream 24) from separator 14 is divided into gaseous first and second streams, 25 and 27. Stream 25, containing about 40 percent of the total vapor, is combined with the separator liquid (stream 28). The combined stream 26 then passes through exchanger 15 in heat exchange relation with the −144° F. cold residue gas stream 29 resulting in cooling and substantial condensation of the combined stream. The substantially condensed stream 26a at −142° F. is then expanded through an appropriate expansion device, such as expansion valve 16, to a pressure of approximately 412 psia, i.e. 5 psi above the operating pressure of the fractionation tower 19. During expansion, the stream is cooled to −144° F. (stream 26b).

In the process illustrated in FIG. 3, the expanded stream 26b reaches a temperature of −144° F. and flows to the heat exchanger 31. The mixed phase stream 26b is warmed in the exchanger to −136° F. and partially vaporized as it provides cooling and substantial condensation of a compressed recycle portion (stream 40a) of distillation stream 39 leaving the top of fractionation tower 19. The warmed stream 26c then enters the distillation column or demethanizer at a lower mid-column feed position. The distillation column is in a lower region of fractionation tower 19.

The substantially condensed stream 40b leaving exchanger 31 is then expanded through an appropriate expansion device, such as expansion valve 33, to the demethanizer operating pressure. During expansion a portion of the stream is vaporized, resulting in cooling of the total stream. In the process illustrated in FIG. 3, the expanded stream 40c leaving expansion valve 33 reaches a temperature of −145° F., and is supplied to the fractionation tower as the top tower feed. The vapor portion of stream 40c combines with the vapors rising from the top fractionation stage of the column to form distillation stream 39, which is withdrawn from an upper region of the tower. This stream is then divided into two streams. One portion, stream 29, is the cold volatile residue gas fraction. The other portion, recycle stream 40, is compressed to a pressure of about 490 psia, i.e. about 83 psi higher than the demethanizer, in cold recycle compressor 32. This compressed recycle stream 40a, now at about −124° F., then flows to heat exchanger 31 where it is cooled and substantially condensed by heat exchange with mixed phase stream 26b.

Returning to gaseous second stream 27, the remaining 60 percent of the vapor from separator 14 enters an expansion device such as work expansion machine 17 in which mechanical energy is extracted from this portion of the high pressure feed. The machine 17 expands the vapor substantially isentropically from a pressure of about 1025 psia to the pressure of the demethanizer (about 407 psia), with the work expansion cooling the expanded stream to a temperature of approximately −74° F. (stream 27a). The expanded and partially condensed stream 27a is supplied as feed to the distillation column at a second mid-column feed point.

The liquid product stream 30 exits the bottom of tower 19 at 72° F. The cold residue gas stream 29 passes countercurrently to stream 26 in heat exchanger 15 where it is heated to −3° F. (stream 29a) as it provides cooling and substantial condensation of stream 26. The partially warmed stream 29a then flows to heat exchanger 12 where it is further warmed to 60° F. (stream 29b) as it provides cooling of stream 21a. The further warmed residue gas stream 29b then flows to heat exchanger 10 where it is heated to 98° F. (stream 29c) as it provides cooling of inlet gas stream 22. The residue gas is then re-compressed in two stages. The first stage of compression is compressor 18 driven by the expansion machine 17. The second stage of compression is compressor 20 driven by a supplemental power source which compresses the residue gas (stream 29d) to the line pressure of 1050 psia.

A summary of stream flow rates and energy consumption for the process illustrated in FIG. 3 is set forth in the following table:

TABLE III (FIG. 3)
Stream Flow Summary - (Lb. Moles/Hr)

| Stream | Methane | Ethane | Propane | Butanes+ | Total |
|---|---|---|---|---|---|
| 21 | 25381 | 1161 | 362 | 332 | 27448 |
| 24 | 25323 | 1149 | 352 | 264 | 27298 |
| 28 | 58 | 12 | 10 | 68 | 150 |
| 25 | 10096 | 458 | 140 | 105 | 10883 |
| 27 | 15227 | 691 | 212 | 159 | 16415 |
| 39 | 31215 | 10 | 0 | 0 | 31414 |
| 40 | 5863 | 2 | 0 | 0 | 5900 |
| 29 | 25352 | 8 | 0 | 0 | 25514 |
| 30 | 29 | 1153 | 362 | 332 | 1934 |

| Recoveries* | |
|---|---|
| Ethane | 99.31% |
| Propane | 100.00% |
| Butanes+ | 100.00% |

TABLE III-continued
(FIG. 3)
Stream Flow Summary - (Lb. Moles/Hr)

| Horsepower | |
|---|---|
| Residue Compression | 12,968 |
| Cold Recycle Compression | 244 |
| Total Horsepower | 13,212 |

*(Based on un-rounded flow rates)

Using the refrigeration available in flash expanded stream 26b to provide cooling and substantial condensation of stream 40a in exchanger 31, it is possible to minimize the horsepower required for compression of the recycle stream. It is necessary to compress the recycle stream 40 only to a pressure at which it can be substantially condensed at a temperature warmer than that of flash expanded stream 26b. Typically this involves raising the pressure of recycle stream 40 by 70-100 psi. This provides a top column feed containing very little ethane and heavier hydrocarbons, which rectifies the vapors stripped from the feeds in the lower portions of the column, thereby reducing the equilibrium losses of ethane and heavier hydrocarbons in the fractionation tower overhead stream 39 and subsequently in the residue gas stream 29.

Comparison of the recovery levels displayed in Tables I and III shows that the present invention improves ethane recovery from 89.80% to 99.31%, propane recovery from 98.16% to 100.00%, and butanes+ recovery from 99.53% to 100.00%. Comparison of Tables I and III further shows that the improvement in yields was not simply the result of increasing the horsepower (utility) requirements. To the contrary, when the present invention is employed, as in Example 1, not only do ethane, propane, and butanes+ recoveries increase over those of the prior art process, but liquid recovery efficiency also increases by 9.3 percent (in terms of ethane recovered per unit of horsepower expended).

Comparing the present invention to the prior art process displayed in FIG. 2, Tables II and III show that the FIG. 2 prior art process essentially matches the recovery levels of the present invention for $C_2+$ components. However, the FIG. 2 process does so at the expense of greatly increased horsepower (utility) consumption. The present invention achieves the same recovery levels using only 76 percent of the external power required by the FIG. 2 prior art process.

Example 2

Figure 4:
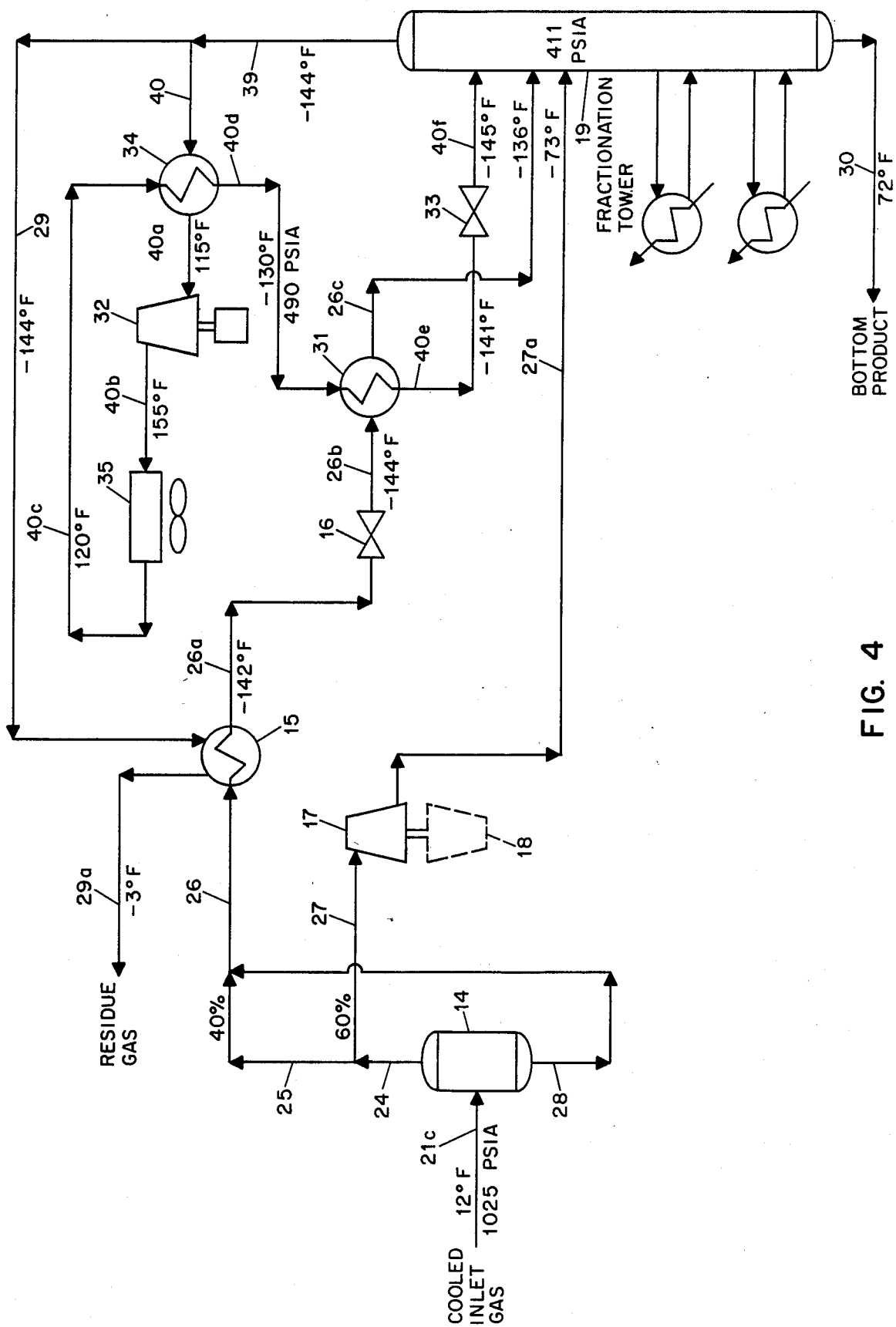
FIGS. 4 and 5 are fragmentary flow diagrams illustrating alternative means of application of the present invention to a natural gas stream.

FIG. 3 represents the preferred embodiment of the present invention for the temperature and pressure conditions shown. Another embodiment of the present invention is illustrated in the fragmentary process flow diagram shown in FIG. 4. In the simulation of the process depicted in FIG. 4, the inlet gas cooling scheme is identical to that used in FIG. 3. The difference lies in the disposition of the recycle stream 40 to be compressed in the compressor 32. Rather than compressing the recycle stream directly into heat exchanger 31, the stream can first be warmed so that cryogenic metallurgy is not required in the compressor. One method of accomplishing this is as shown in FIG. 4, where the recycle vapor stream 40 enters cross exchanger 34 and is heated to 115° F. by heat exchange with the warm recycle compressor discharge stream 40c. The warm stream 40a enters the warm recycle compressor 32 and is compressed to about 500 psia (stream 40b). The compressed stream is then cooled to 120° F. in heat exchanger 35 (stream 40c). After cross exchange with the cool stream 40, stream 40d at −130° F. enters exchanger 31 where it is cooled and substantially condensed by heat exchange with the mixed phase stream 26b as discussed previously. The substantially condensed stream 40e is then flash expanded in expansion valve 33. The cold, flash expanded stream 40f, now at about −145° F., is supplied as the top feed to fractionation tower 19.

A summary of stream flow rates and energy consumption for the process illustrated in FIG. 4 is set forth in the following table:

TABLE IV
(FIG. 4)
Stream Flow Summary - (Lb. Moles/Hr)

| Stream | Methane | Ethane | Propane | Butanes+ | Total |
|---|---|---|---|---|---|
| 21c | 25381 | 1161 | 362 | 332 | 27448 |
| 24 | 25323 | 1149 | 352 | 264 | 27298 |
| 28 | 58 | 12 | 10 | 68 | 150 |
| 25 | 10096 | 458 | 140 | 105 | 10883 |
| 27 | 15227 | 691 | 212 | 159 | 16415 |
| 39 | 31217 | 10 | 0 | 0 | 31406 |
| 40 | 5864 | 2 | 0 | 0 | 5900 |
| 29 | 25353 | 8 | 0 | 0 | 25506 |
| 30 | 28 | 1153 | 362 | 332 | 1942 |

| Recoveries* | |
|---|---|
| Ethane | 99.31% |
| Propane | 100.00% |
| Butanes+ | 100.00% |
| Horsepower | |
| Residue Compression | 12,742 |
| Warm Recycle Compression | 770 |
| Total Horsepower | 13,512 |

*(Based on unrounded flow rates)

A comparison of Tables III and IV show that the FIG. 4 embodiment of the present invention can maintain high recovery levels with a slight increase in the horsepower (utility) requirements. The choice between compressing stream 40 cold or warm depends on factors such as plant size and available equipment.

Example 3

Figure 5:
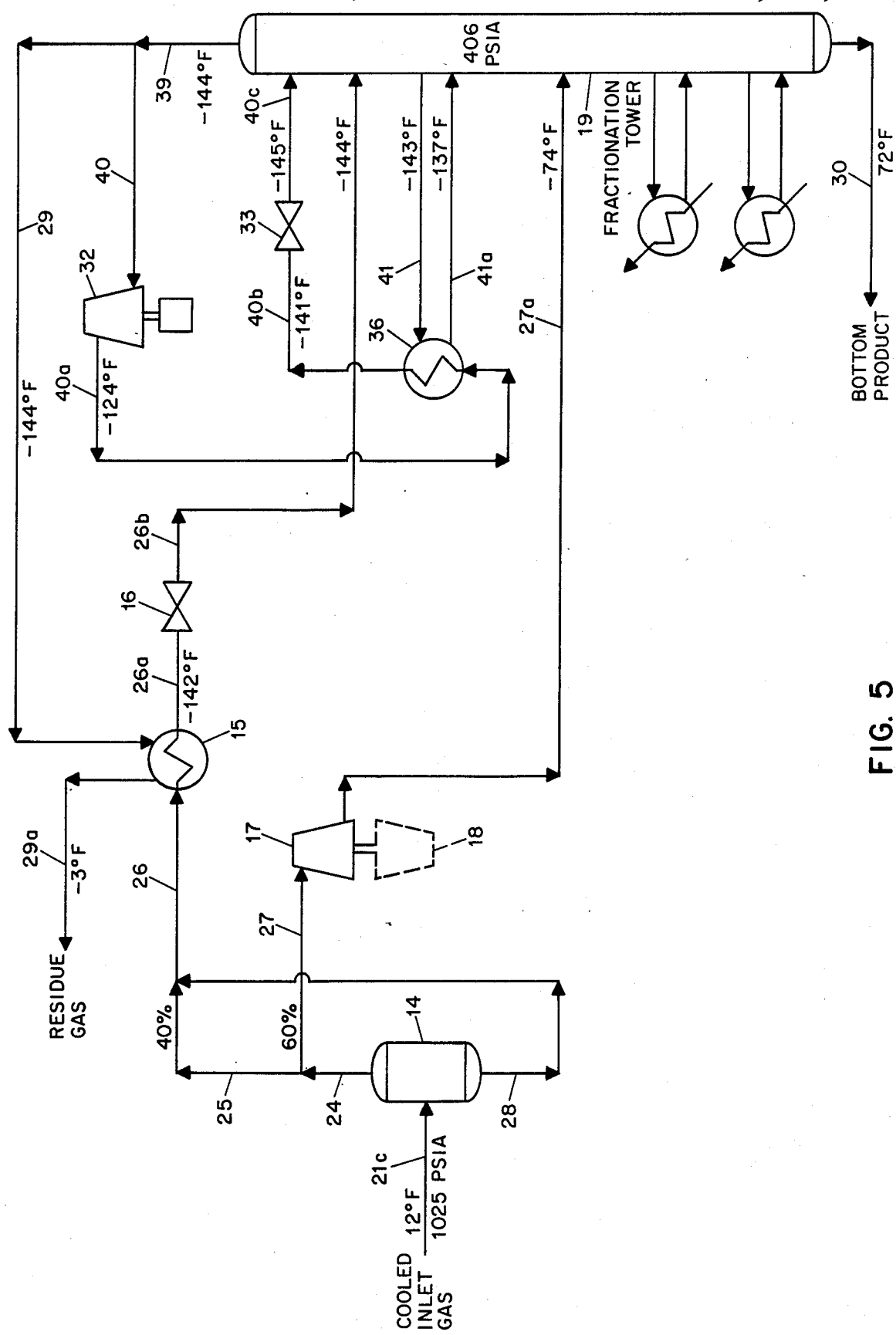

A third embodiment of the present invention is illustrated in the fragmentary flow diagram shown in FIG. 5. In the simulation of the process depicted in FIG. 5, the inlet gas cooling scheme is identical to that used in FIG. 3 and FIG. 4. The difference lies in the method used to cool and substantially condense the compressed recycle stream (40a). In the embodiment of FIG. 5, the compressed stream 40a is cooled and substantially condensed in exchanger 36 which functions as a side reboiler to the demethanizer. Cooling is provided by a liquid stream withdrawn from the distillation column in fractionation tower 19, stream 41, at a temperature of −143° F. This liquid stream is heated and partially vaporized in exchanger 36 and the mixed phase stream 41a, now at −137° F., is returned to the distillation column. The substantially condensed recycle stream 40b from exchanger 36 is at a temperature of −141° F. and is flash expanded to the operating pressure at the fractionation tower in expansion valve 33. The flash expanded stream 40c, now at about −145° F., enters fractionation tower 19 at its top most feed point.

Because stream 26b from expansion valve 16 is not used to provide cooling of the compressed recycle stream 40a, this mixed phase stream flows directly to distillation column at a middle column feed position.

A summary of stream flow rates and energy consumption for the process illustrated in FIG. 5 is set forth in the following table:

TABLE V
(FIG. 5)
Stream Flow Summary - (Lb. Moles/Hr)

| Stream | Methane | Ethane | Propane | Butanes+ | Total |
|---|---|---|---|---|---|
| 21c | 25381 | 1161 | 362 | 332 | 27448 |
| 24 | 25323 | 1149 | 352 | 264 | 27298 |
| 28 | 58 | 12 | 10 | 68 | 150 |
| 25 | 10096 | 458 | 140 | 105 | 10883 |
| 27 | 15227 | 691 | 212 | 159 | 16415 |
| 39 | 31216 | 10 | 0 | 0 | 31415 |
| 40 | 5863 | 2 | 0 | 0 | 5900 |
| 29 | 25353 | 8 | 0 | 0 | 25515 |
| 30 | 28 | 1153 | 362 | 332 | 1933 |

| Recoveries* | |
|---|---|
| Ethane | 99.32% |
| Propane | 100.00% |
| Butanes+ | 100.00% |
| Horsepower | |
| Residue Compression | 13,008 |
| Cold Recycle Compression | 247 |
| Total Horsepower | 13,255 |

*(Based on un-rounded flow rates)

A comparison of Tables III and V shows that the embodiment of FIG. 5 is only slightly less efficient than that of FIG. 3.

It should also be noted that stream 28 in FIG. 5 need not be combined with stream 25. Alternatively, all or a portion of stream 28 may be expanded to the operating pressure of the column and then supplied to the column at a mid-column feed position.

Example 4

Figure 6:
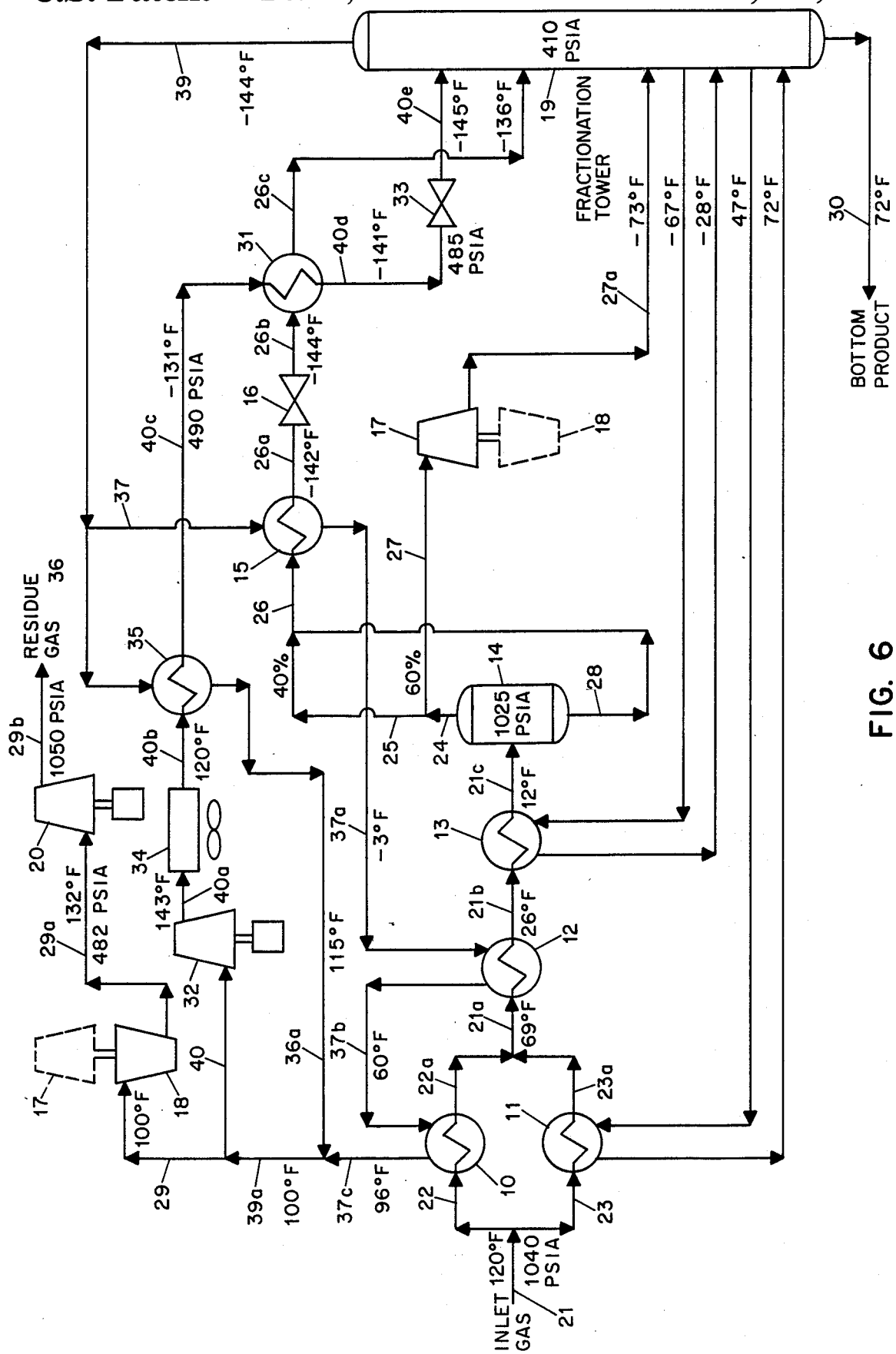
FIGS. 6, 7 and 8 are flow diagrams of additional natural gas processing plants in accordance with the present invention.

A fourth embodiment of the present invention is shown in FIG. 6. The feed gas composition and conditions considered in the process illustrated in FIG. 6 are the same as those in FIGS. 1 through 5.

In the simulation of the process of FIG. 6, the inlet gas cooling and expansion scheme is identical to that used in FIG. 3. The difference lies in where the gas stream to be compressed, substantially condensed and used as top tower feed to the demethanizer is withdrawn from the distillation stream 39. Referring to FIG. 6, the warmed distillation stream 39a is divided into two streams, 29 and 40. Stream 29 is the residue gas fraction which is re-compressed in two stages as previously discussed. Stream 40 is the recycle stream which is compressed in warm recycle compressor 32 to about 500 psia, i.e. 90 psi above the operating pressure of the demethanizer. The compressed stream 40a is cooled to 120° F. (stream 40b) in exchanger 34. (Depending on the temperature of the stream following compression, exchanger 34 may not be necessary.) The cooled stream 40b is then further cooled in exchanger 35 to a temperature of about −131° F. (stream 40c) by heat exchange with a portion (stream 36) of distillation stream 39. The further cooled stream 40c then enters exchanger 31 where it is substantially condensed by heat exchange with the mixed phase stream 26b from expansion valve 16 as discussed previously for FIG. 3. The substantially condensed stream 40d is then flash expanded in expansion valve 33 and the expanded stream 40e flows as top feed at −145° F. to fractionation tower 19.

Distillation stream 39 leaves the upper region of the tower at −144° F. and is then divided into two portions. One portion, stream 37, is warmed to about 96° F. (stream 37c) as it provides cooling of the inlet feed in exchangers 15, 12 and 10. The other portion, stream 36, provides cooling of the compressed recycle stream 40b in the exchanger 35 as discussed previously. The thus warmed streams 36a and 37c recombine as the warmed fractionation tower overhead stream 39a which is then divided as described above.

A summary of the stream flow rates and energy consumption for the process illustrated in FIG. 6 is set forth in the following table:

TABLE VI
(FIG. 6)
Stream Flow Summary - (Lb. Moles/Hr)

| Stream | Methane | Ethane | Propane | Butanes+ | Total |
|---|---|---|---|---|---|
| 21 | 25381 | 1161 | 362 | 332 | 27448 |
| 24 | 25323 | 1149 | 352 | 264 | 27298 |
| 28 | 58 | 12 | 10 | 68 | 150 |
| 25 | 10096 | 458 | 140 | 105 | 10883 |
| 27 | 15227 | 691 | 212 | 159 | 16415 |
| 39 | 31119 | 10 | 0 | 0 | 31302 |
| 40 | 5766 | 2 | 0 | 0 | 5800 |
| 29 | 25353 | 8 | 0 | 0 | 25502 |
| 30 | 28 | 1153 | 362 | 332 | 1946 |

| Recoveries* | |
|---|---|
| Ethane | 99.33% |
| Propane | 100.00% |
| Butanes+ | 100.00% |
| Horsepower | |
| Residue Compression | 12,754 |
| Warm Recycle Compression | 833 |
| Total Horsepower | 13,587 |

*(Based on un-rounded flow rates)

A comparison of Tables III and VI shows that the FIG. 6 embodiment of the present invention can also maintain high recovery levels with only a slight increase in horsepower (utility) consumption. The choice of where to withdraw recycle stream 40 in the process depends on factors which include plant size and available equipment.

Alternatively, the process of the invention can be operated to attain less than maximum recoveries. If this is desired, the flow rate of recycle stream 40 is reduced, thus reducing the quantity of top column feed to fractionation tower 19 in FIG. 3. As this flow rate is reduced, less reflux liquid is available for the column resulting in a warmer column overhead temperature. Ethane recovery then decreases. This is illustrated in the following example.

Example 5

Figure 10:
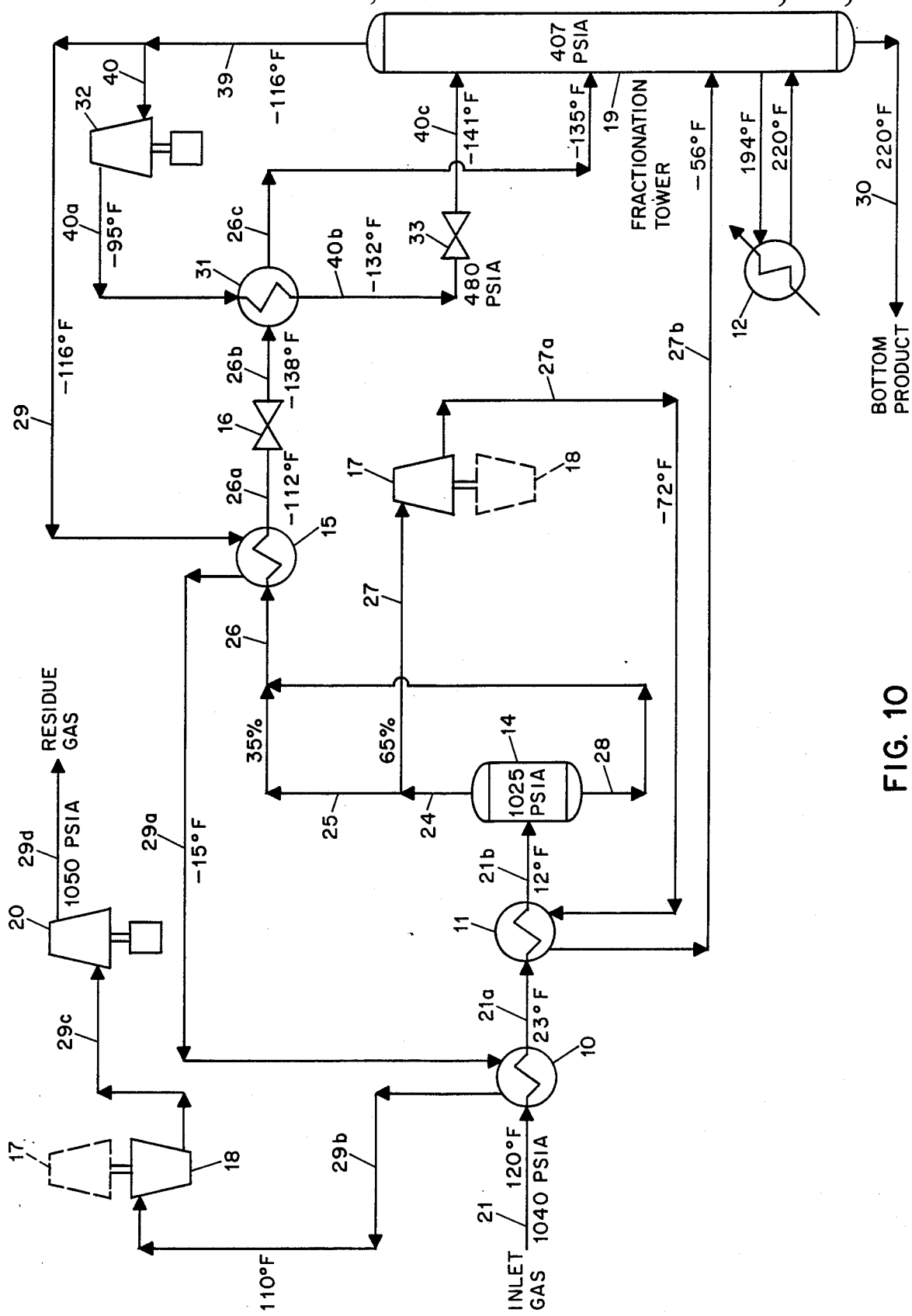
FIG. 10 is a flow diagram illustrating an alternative means of application of the present invention to a natural gas stream from which recovery of propane and heavier hydrocarbons is desired.

The process of the present invention is also applicable for processing gas streams when it is desirable to recover only the $C_3$ components and heavier hydrocarbon components (rejection of $C_2$ components and lighter components to the residue gas). Such an embodiment of the present invention is shown in FIG. 10. The feed gas composition and conditions considered in the process of FIG. 10 are the same as those in FIGS. 1 through 6. Because of the warmer process operating conditions associated with propane recovery (ethane rejection) operation, the inlet gas cooling scheme is slightly different than for the ethane recovery cases discussed previously.

Referring to FIG. 10, inlet gas enters the process at 120° F. and 1040 psia as stream 21. This stream is cooled to 23° F. (stream 21a) by heat exchange with cool residue gas at −15° F. (stream 29a) in exchanger 10. From this exchanger, stream 21a is further cooled to 12° F.

(stream 21b) by the expander outlet stream 27a. The feed stream 21b then enters the high pressure separator 14 at 1025 psia where the vapor (stream 24) is separated from the condensed liquid (stream 28).

The vapor (stream 24) from separator 14 is divided into gaseous first and second streams, 25 and 27. Stream 25, containing about 35 percent of the total vapor, is combined with the separator liquid (stream 28). The combined stream 26 then passes through heat exchanger 15 in heat exchange relation with the −116° F. cold residue gas fraction 29 resulting in cooling and substantial condensation of the combined stream. The substantially condensed stream 26a at −112° F. is then expanded through an appropriate expansion device, such as an expansion valve 16, to a pressure of approximately 412 psia. During expansion, a portion of the stream will vaporize, resulting in cooling of the total stream.

In the process illustrated in FIG. 10, the expanded stream 26b reaches a temperature of −138° F. and flows to the heat exchanger 31. The mixed phase stream 26b is warmed in the exchanger to −135° F. and partially vaporized as it provides cooling, resulting in substantial condensation of a portion (stream 40a) of distillation stream 39 leaving the top of tower 19. The warmed stream 26c then enters the deethanizer distillation column in fractionation tower 19 at a mid-column feed position.

The substantially condensed stream 40b leaving exchanger 31 is then expanded through an appropriate expansion device, such as expansion valve 33, to the deethanizer operating pressure. During expansion a portion of the stream is vaporized, resulting in cooling of the total stream. In the process illustrated in FIG. 10, the expanded stream 40c leaving expansion valve 33 reaches a temperature of −141° F., and is supplied to the fractionation tower as the top feed. The vapor portion of stream 40c combines with the vapors rising form the top fractionation stage of the column to form distillation stream 39, which exits the top of the tower. This stream is then divided into two streams. One portion, stream 29, is the volatile residue gas fraction. The other portion, recycle stream 40, is compressed to a pressure of about 485 psia, i.e. about 78 psi higher than the deethanizer, in cold recycle compressor 32. This compressed stream 40a, now at about −95° F., then flows to heat exchanger 31 where it is cooled and substantially condensed by heat exchange with mixed phase stream 26b.

Returning to gaseous second stream 27, the remaining 65 percent of the vapor from separator 14 enters an expansion device such as work expansion machine 17 as described in earlier cases. The expansion machine 17 expands the vapor to a pressure of about 412 psia thereby cooling the expanded stream to a temperature of −72° F. (stream 27a). The expanded and partially condensed stream 27a then flows to exchanger 11 where it is warmed as it provides cooling of the inlet gas stream. The warm expanded stream 27b, now at a temperature of about −56° F., is then supplied to the deethanizer at a second mid-column feed position.

The deethanizer includes a reboiler 12 which heats and vaporizes a portion of the liquids flowing down the column to provide the stripping vapors which flow up the column. When operating as a deethanizer (ethane rejection), the tower reboiler temperatures are significantly warmer than when operating as a demethanizer (ethane recovery). Generally this makes it impossible to reboil the tower using plant inlet feed as is typically done for ethane recovery operation. Therefore, an external source for reboil heat is normally employed.

The liquid product stream 30 exits the bottom of the tower at 220° F., based on a typical specification of an ethane to propane ratio of 0.025:1 on a molar basis in this liquid product. The cold distillation overhead stream 39 exits the column at about −116° F. and is divided into two streams (29 and 40), as discussed above. The cold residue gas stream 29 is warmed to about 110° F. as it provides cooling of the inlet gas stream in exchangers 15 and 10. It is then compressed in two stages by compressor 18, driven by expansion machine 17, and compressor 20, driven by a supplemental power source.

A summary of the stream flow rates and energy consumption for the process illustrated in FIG. 10 is set forth in the following table:

TABLE VII (FIG. 10)
Stream Flow Summary - (Lb. Moles/Hr)

| Stream | Methane | Ethane | Propane | Butanes+ | Total |
|---|---|---|---|---|---|
| 21 | 25381 | 1161 | 362 | 332 | 27448 |
| 24 | 25323 | 1149 | 352 | 264 | 27298 |
| 28 | 58 | 12 | 10 | 68 | 150 |
| 25 | 8863 | 402 | 123 | 92 | 9554 |
| 27 | 16460 | 747 | 229 | 172 | 17744 |
| 39 | 27754 | 1260 | 0 | 0 | 29245 |
| 40 | 2373 | 108 | 0 | 0 | 2500 |
| 29 | 25381 | 1152 | 0 | 0 | 26745 |
| 30 | 0 | 9 | 362 | 332 | 703 |

| Recoveries* | |
|---|---|
| Ethane | less than 1% |
| Propane | 99.90% |
| Butanes+ | 100.00% |
| Horsepower | |
| Residue Compression | 13,562 |
| Cold Recycle Compression | 120 |
| Total Horsepower | 13,682 |

*(Based on un-rounded flow rates)

As can be seen from the above table, more than 99 percent of the ethane is rejected to the residue gas stream while still maintaining in excess of 99.9 percent propane recovery. This requires a lesser quantity of recycle stream 40 than was used for ethane recovery operation.

Although it is not necessarily the optimum approach, it should also be recognized that the flow scheme presented in FIG. 10 can also be employed when ethane ($C_2$ component) recovery is desired.

Other Embodiments

The high pressure liquid stream 28 in FIGS. 3 through 6 and 10 need not be combined with the portion of the separator vapor (stream 25) flowing to exchanger 15. Alternatively, stream 28 (or a portion thereof) may be expanded through an appropriate expansion device, such as an expansion valve or expansion machine, and fed to a third mid-column feed point on the distillation column. Stream 28 may also be used for inlet gas cooling or other heat exchange service before or after the expansion step prior to flowing to the demethanizer.

Figure 9:
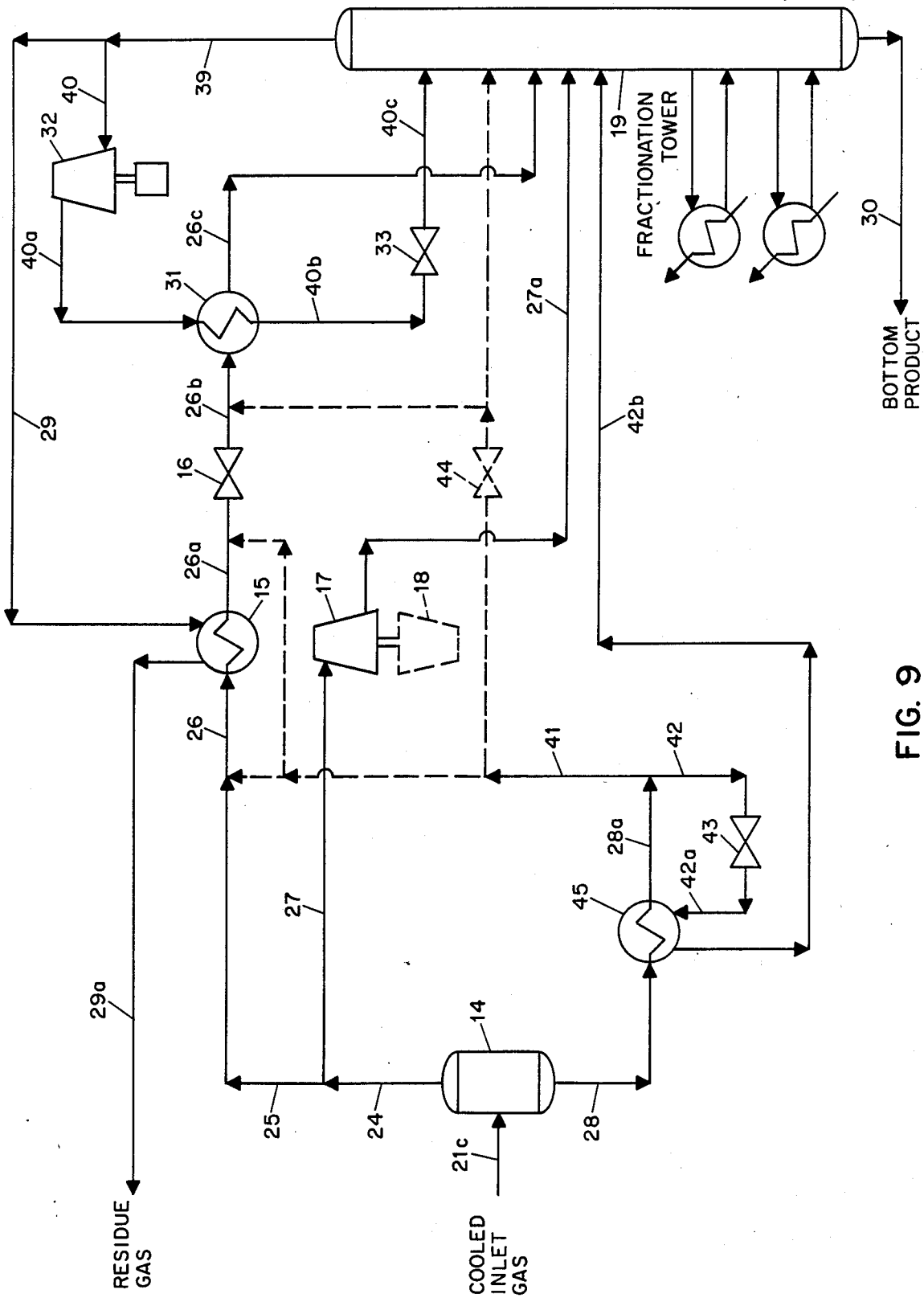
FIG. 9 is a fragmentary flow diagram showing a natural gas processing plant in accordance with the present invention for a richer gas stream.

In instances where the inlet gas is richer than that heretofore described, an embodiment such as that depicted in FIG. 9 may be employed. Condensed stream 28 flows through exchanger 45 where it is subcooled by heat exchange with the cooled stream 42a from expansion valve 43. The subcooled liquid (stream 28a) is then divided into two portions. The first portion (stream 42)

flows through expansion valve 43 where it undergoes expansion and flash vaporization as the pressure is reduced to about the pressure of the fractionation tower. The cold stream 42a from expansion valve 43 then flows through exchanger 45, where it is used to subcool the liquids from separator 14. From exchanger 45 the stream 42b flows to the distillation column in fractionation tower 19 as a lower mid-column feed. The second liquid portion, stream 41, still at high pressure, is either: (1) combined with portion 25 of the vapor stream from separator 14, (2) combined with substantially condensed stream 26a, or (3) expanded in expansion valve 44 and thereafter either supplied to the distillation column at an upper mid-column feed position or combined with expanded stream 26b. Alternatively, portions of stream 41 may follow more than one and indeed all of the flow paths heretofore described and depicted in FIG. 9.

Figure 7:
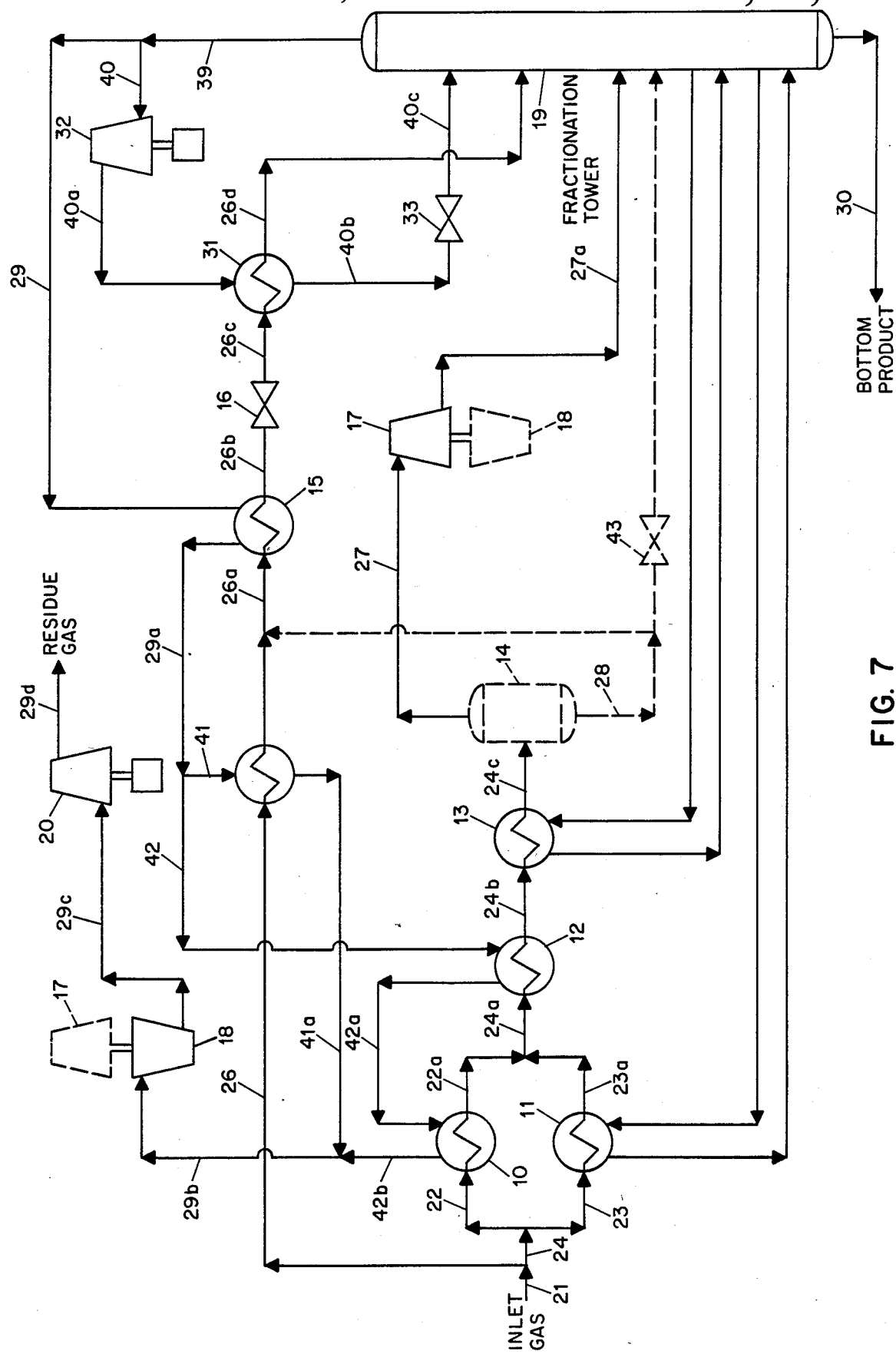
Figure 8:
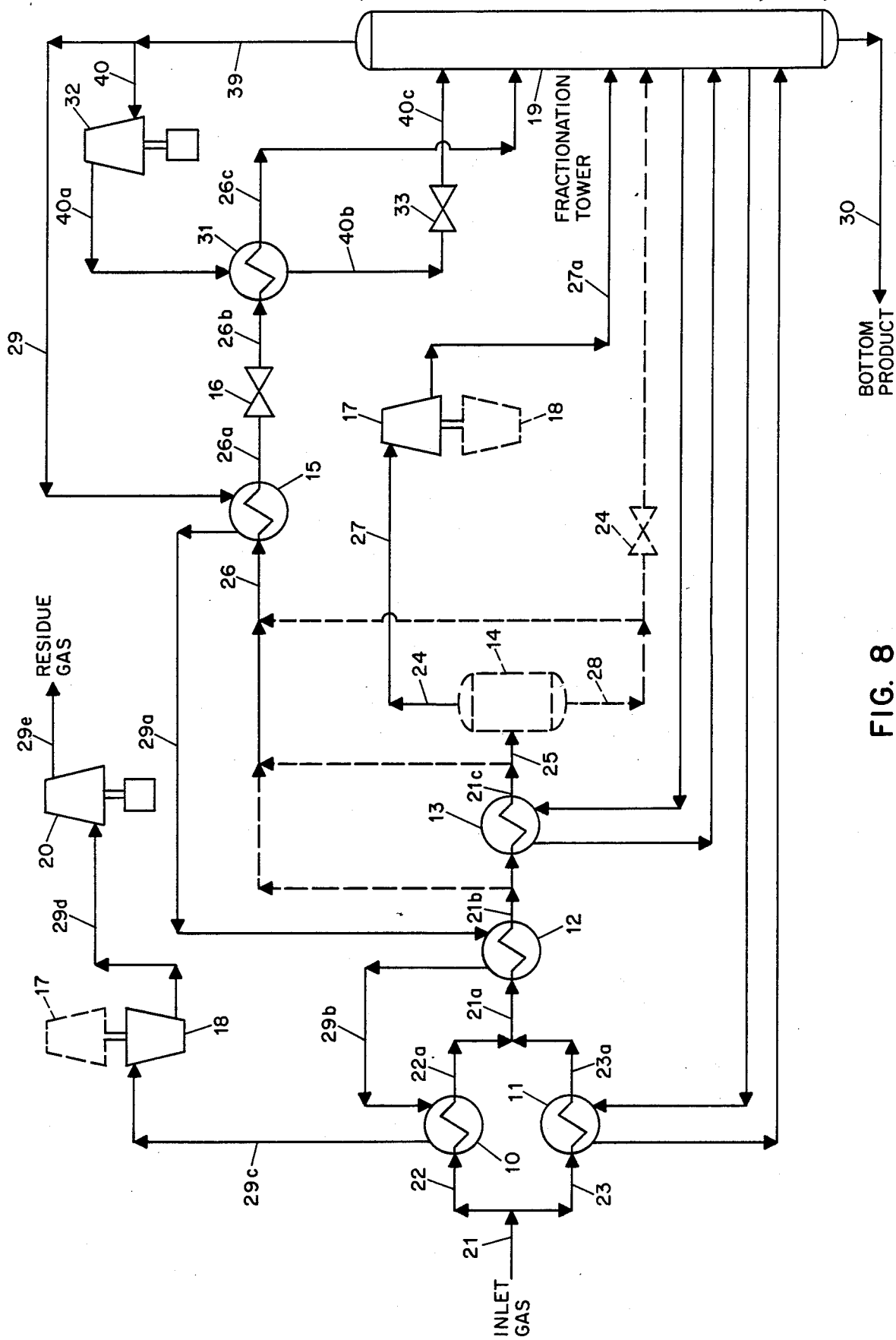

In accordance with this invention, the splitting of the vapor feed may be accomplished in several ways. In the processes of FIGS. 3 through 6, 9 and 10, the splitting of vapor occurs following cooling and separation of any liquids which may have been formed. The high pressure gas may be split, however, prior to any cooling of the inlet gas as shown in FIG. 7 or after the cooling of the gas and prior to any separation stages as shown in FIG. 8. In some embodiments, vapor splitting may be effected in a separator. Alternatively, the separator 14 in the processes shown in FIGS. 7 and 8 may be unnecessary if the inlet gas is relatively lean. Moreover, the use of external refrigeration to supplement the cooling available to the inlet gas from other process streams may be employed, particularly in the case of an inlet gas richer than that used in Example 1. The use and distribution of demethanizer liquids for process heat exchanger, and the particular arrangement of heat exchangers for inlet gas cooling must be evaluated for each particular application, as well as the choice of process streams for specific heat exchange services. For example, the second stream depicted in FIG. 8, stream 25, may be cooled after division of the inlet stream and prior to expansion of the second stream.

It will also be recognized that the relative amount of feed found in each branch of the split vapor feed will depend on several factors, including feed gas pressure, feed gas composition, the amount of heat which can economically be extracted from the feed and the quantity of horsepower available. More feed to the top of the column may increase recovery while decreasing power recovered from the expander thereby increasing the recompression horsepower requirements. Increasing feed lower in the column reduces the horsepower consumption but may also reduce product recovery. The mid-column feed positions depicted in FIGS. 3 through 6 and 10 are the preferred feed locations for the process operating conditions described. However, the relative locations of the mid-column feeds may vary depending on inlet composition of other factors such as desired recovery levels and amount of liquid formed during inlet gas cooling. Moreover, two or more of the feed streams, or portions thereof, may be combined depending on the relative temperatures and quantities of the individual streams, and the combined stream then fed to a mid-column feed position. FIGS. 3 through 6 and 10 are the preferred embodiments for the compositions and pressure conditions shown. Although individual stream expansion is depicted in particular expansion devices, alternative expansion means may be employed where appropriate. For example, conditions may warrant work expansion of the substantially condensed portion of the feed stream (26a in FIG. 3) or the substantially condensed recycle stream (40b in FIG. 3).

The embodiments shown in FIGS. 3 through 9 can also be used when it is desirable to recover only the $C_3$ components and heavier components $C_2$ component rejection). This is accomplished by appropriate adjustment of the column feed rates and conditions.

While there have been described what are believed to be preferred embodiments of the invention, those skilled in the art will recognize that other and further modifications may be made thereto, e.g. to adapt the invention to various conditions, types of feed, or other requirements without departing from the spirit of the present invention as defined by the following claims:

I claim:

1. In a process for the separation of a gas containing methane, $C_2$ components, $C_3$ components and heavier hydrocarbon components into a volatile residue gas fraction containing a major portion of said methane and a relatively less volatile fraction containing a major portion of said $C_2$ components, $C_3$ components and heavier components, in which process
    (a) said gas is cooled under pressure to provide a cooled stream;
    (b) said cooled stream is expanded to a lower pressure whereby it is further cooled; and
    (c) said further cooled stream is fractionated at said lower pressure whereby the major portion of said $C_2$ components, $C_3$ components and heavier hydrocarbon components is recovered in said relatively less volatile reaction;
    the improvement wherein said gas is cooled sufficiently to partially condense it; and
    (1) said partially condensed gas is separated thereby to provide a vapor stream and a condensed stream;
    (2) said vapor stream is thereafter divided into gaseous first and second streams;
    (3) said gaseous first stream is combined with at least a portion of said condensed stream to form a combined stream and said combined stream is cooled to condense substantially all of it and is thereafter expanded to said lower pressure whereby it is further cooled;
    (4) the expanded cooled combined stream is then directed in heat exchange relation with a warmer compressed recycle portion of a distillation stream which rises in a fractionation tower; the distillation stream is withdrawn from an upper region of said tower and is thereafter divided into said volatile residue gas fraction and said recycle stream;
    (5) said combined stream is thereafter supplied at a first mid-column feed position to a distillation column in a lower region of the fractionation tower;
    (6) said compressed recycle stream is cooled by said expanded cooled stream sufficiently to substantially condense it;
    (7) said substantially condensed compressed recycle stream is expanded to said lower pressure and supplied to said fractionation tower at a top feed position;
    (8) said gaseous second stream is expanded to said lower pressure and is supplied to said distillation column at a second mid-column feed position; and
    (9) the pressure of said compressed recycle stream and the quantities and temperatures of said feeds to the column are effective to maintain tower overhead temperature at a temperature whereby the major portion of said $C_2$ components, $C_3$ components and heavier hydrocarbon components is recovered in said relatively less volatile fraction.

2. In a process for the separation of a gas containing methane, $C_2$ components, $C_3$ components and heavier hydrocarbon components into a volatile residue gas fraction containing a major portion of said methane and said $C_2$ components and a relatively less volatile fraction containing a major portion of said $C_3$ components and heavier components, in which process
   (a) said gas is cooled under pressure to provide a cooled stream;
   (b) said cooled stream is expanded to a lower pressure whereby it is further cooled; and
   (c) said further cooled stream is fractionated at said lower pressure whereby the major portion of said $C_3$ components and heavier hydrocarbon components is recovered in said relatively less volatile fraction;

the improvement wherein said gas is cooled sufficiently to partially condense it; and
   (1) said partially condensed gas is separated thereby to provide a vapor stream and a condensed stream;
   (2) said vapor stream is thereafter divided into gaseous first and second streams;
   (3) said gaseous first stream is combined with at least a portion of said condensed stream to form a combined stream and said combined stream is cooled to condense substantially all of it and is thereafter expanded to said lower pressure whereby it is further cooled;
   (4) the expanded cooled combined stream is then directed in heat exchange relation with a warmer compressed recycle portion of a distillation stream which rises in a fractionation tower; the distillation stream is withdrawn from an upper region of said tower and is thereafter divided into said volatile residue gas fraction and said recycle stream;
   (5) said combined stream is thereafter supplied at a first mid-column feed position to a distillation column in a lower region of the fractionation tower;
   (6) said compressed recycle stream is cooled by said expanded cooled combined stream sufficiently to substantially condense it;
   (7) said substantially condensed compressed recycle stream is expanded to said lower pressure and supplied to said fractionation tower at a top feed position;
   (8) said gaseous second stream is expanded to said lower pressure and is supplied to said distillation column at a second mid-column feed position; and
   (9) the pressure of said compressed recycle stream and the quantities and temperatures of said feeds to the column are effective to maintain tower overhead temperature at a temperature whereby the major portion of said $C_3$ components and heavier hydrocarbon components is recovered in said relatively less volatile fraction.

3. In a process for the separation of a gas containing methane, $C_2$ components, $C_3$ components and heavier hydrocarbon components into a volatile residue gas fraction containing a major portion of said methane and a relatively less volatile fraction containing a major portion of said $C_2$ components, $C_3$ components and heavier components, in which process
   (a) said gas is cooled under pressure to provide a cooled stream;
   (b) said cooled stream is expanded to a lower pressure whereby it is further cooled; and
   (c) said further cooled stream is fractionated at said lower pressure whereby the major portion of said $C_2$ components, $C_3$ components and heavier hydrocarbon components is recovered in said relatively less volatile fraction;

the improvement wherein prior to cooling, said gas is divided into gaseous first and second streams; and
   (1) said gaseous second stream is cooled under pressure sufficiently to partially condense it;
   (2) said partially condensed second stream is separated thereby to provide a vapor stream and a condensed stream;
   (3) said gaseous first stream is cooled and then combined with at least a portion of said condensed stream to form a combined stream and said combined stream is cooled to condense substantially all of it and is thereafter expanded to said lower pressure whereby it is further cooled;
   (4) the expanded cooled combined stream is then directed in heat exchange relation with a warmer compressed recycle portion of a distillation stream which rises in a fractionation tower; the distillation stream is withdrawn from an upper region of said tower and is thereafter divided into said volatile residue gas fraction and said recycle stream;
   (5) said combined stream is thereafter supplied at a first mid-column feed position to a distillation column in a lower region of the fractionation tower;
   (6) said compressed recycle stream is cooled by said expanded cooled combined stream sufficiently to substantially condense it;
   (7) said substantially condensed compressed recycle stream is expanded to said lower pressure and supplied to said fractionation tower at a top feed position;
   (8) said vapor stream is expanded to said lower pressure and supplied to said distillation column at a second mid-column feed position; and
   (9) the pressure of said compressed recycle stream and the quantities and temperatures of said feeds to the column are effective to maintain the tower overhead temperature at a temperature whereby the major portion of said $C_2$ components, $C_3$ components and heavier hydrocarbon components is recovered in said relatively less volatile fraction.

4. In a process for the separation of a gas containing methane, $C_2$ components, $C_3$ components and heavier hydrocarbon components into a volatile residue gas fraction containing a major portion of said methane and said $C_2$ components and a relatively less volatile fraction containing a major portion of said $C_3$ components and heavier components, in which process
   (a) said gas is cooled under pressure to provide a cooled stream;
   (b) said cooled stream is expanded to a lower pressure whereby it is further cooled; and
   (c) said further cooled stream is fractionated at said lower pressure whereby the major portion of said $C_3$ components and heavier hydrocarbon components is recovered in said relatively less volatile fraction;

the improvement wherein prior to cooling, said gas is divided into gaseous first and second streams; and
   (1) said gaseous second stream is cooled under pressure sufficiently to partially condense it;

(2) said partially condensed second stream is separated thereby to provide a vapor stream and a condensed stream;

(3) said gaseous first stream is cooled and then combined with at least a portion of said condensed stream to form a combined stream and said combined stream is cooled to condense substantially all of it and is thereafter expanded to said lower pressure whereby it is further cooled;

(4) the expanded cooled combined stream is then directed in heat exchange relation with a warmer compressed recycle portion of a distillation stream which rises in a fractionation tower; the distillation stream is withdrawn from an upper region of said tower and is thereafter divided into said volatile residue gas fraction and said recycle stream;

(5) said combined stream is thereafter supplied at a first mid-column feed position to a distillation column in a lower region of the fractionation tower;

(6) said compressed recycle stream is cooled by said expanded cooled combined stream sufficiently to substantially condense it;

(7) said substantially condensed compressed recycle stream is expanded to said lower pressure and supplied to said fractionation tower at a top feed position;

(8) said vapor stream is expanded to said lower pressure and supplied to said distillation column at a second mid-column feed position; and (9) the pressure of said compressed recycle stream and the quantities and temperatures of said feeds to the column are effective to maintain the tower overhead temperature at a temperature whereby the major portion of said $C_3$ components and heavier hydrocarbon components is recovered in said relatively less volatile fraction.

5. In a process for the separation of a gas containing methane, $C_2$ components, $C_3$ components and heavier hydrocarbon components into a volatile residue gas fraction containing a major portion of said methane and a relatively less volatile fraction containing a major portion of said $C_2$ components, $C_3$ components and heavier components, in which process (a) said gas is cooled under pressure to provide a cooled stream;

(b) said cooled stream is expanded to a lower pressure whereby it is further cooled; and (c) said further cooled stream is fractionated at said lower pressure whereby the major portion of said $C_2$ components, $C_3$ components and heavier hydrocarbon components is recovered in said relatively less volatile fraction;

the improvement wherein following cooling; said cooled stream is divided into first and second stream; and (1) said second stream is cooled sufficiently to partially condense it;

(2) said partially condensed second stream is separated thereby to provide a vapor stream and a condensed stream;

(3) said first stream is combined with at least a portion of said condensed stream to form a combined stream and said combined stream is cooled to condense substantially all of it and is thereafter expanded to said lower pressure whereby it is further cooled;

(4) said expanded cooled combined stream is directed in heat exchange relation with a warmer compressed recycle portion of a distillation stream which rises in a fractionation tower; the distillation stream is withdrawn from an upper region of said tower and is thereafter divided into said volatile residue gas fraction and said recycle stream;

(5) said combined stream is thereafter supplied at a first mid-column feed position to a distillation column in a lower region of the fractionation tower;

(6) said compressed recycle stream is cooled by said expanded cooled combined stream sufficiently to substantially condense it;

(7) said substantially condensed compressed recycle stream is expanded to said lower pressure and thereafter supplied to said fractionation tower at a top feed position;

(8) said vapor stream is expanded to said lower pressure and supplied to said distillation column at a second mid-column feed position; and (9) the pressure of said compressed recycle stream and the quantities and temperatures of said feeds to the column are effective to maintain tower overhead temperature at a temperature whereby the major portion of said $C_2$ components, $C_3$ components and heavier hydrocarbon components is recovered in said relatively less volatile fraction.

6. In a process for the separation of a gas containing methane, $C_2$ components, $C_3$ components and heavier hydrocarbon components into a volatile residue gas fraction containing a major portion of said methane and said $C_2$ components and a relatively less volatile fraction containing a major portion of said $C_3$ components and heavier components, in which process (a) said gas is cooled under pressure to provide a cooled stream;

(b) said cooled stream is expanded to a lower pressure whereby it is further cooled; and (c) said further cooled stream is fractionated at said lower pressure whereby the major portion of said $C_3$ components and heavier hydrocarbon components is recovered in said relatively less volatile fraction;

the improvement wherein following cooling, said cooled stream is divided into first and second streams; and (1) said second stream is cooled sufficiently to partially condense it;

(2) said partially condensed second stream is separated thereby to provide a vapor stream and a condensed stream;

(3) said first stream is combined with at least a portion of said condensed stream to form a combined stream and said combined stream is cooled to condense substantially all of it and is thereafter expanded to said lower pressure whereby it is further cooled;

(4) said expanded cooled combined stream is directed in heat exchange relation with a warmer compressed recycle portion of a distillation stream which rises in a fractionation tower; the distillation stream is withdrawn from an upper region of said tower and is thereafter divided into said volatile residue gas fraction and said recycle stream;

(5) said combined stream is thereafter supplied at a first mid-column feed position to a distillation column in a lower region of the fractionation tower;

(6) said compressed recycle stream is cooled by said expanded cooled combined stream sufficiently to substantially condense it;

(7) said substantially condensed compressed recycle stream is expanded to said lower pressure and thereafter supplied to said fractionation tower at a top feed position;

(8) said vapor stream is expanded to said lower pressure and supplied to said distillation column at a second mid-column feed position; and (9) the pressure of said compressed recycle stream and the quantities and temperatures of said feeds to the column are effective to maintain tower overhead temperature at a temperature whereby the major portion of said $C_3$ components and heavier hydrocarbon components is recovered in said relatively less volatile fraction.

7. In a process for the separation of a gas containing methane, $C_2$ components, $C_3$ components and heavier hydrocarbon components into a volatile residue gas fraction containing a major portion of said methane and a relatively less volatile fraction containing a major portion of said $C_2$ components, $C_3$ components and heavier components, in which process (a) said gas is cooled under pressure to provide a cooled stream;

(b) said cooled stream is expanded to a lower pressure whereby it is further cooled; and (c) said further cooled stream is fractionated at said lower pressure whereby the major portion of said $C_2$ components, $C_3$ components and heavier hydrocarbon components is recovered in said relatively less volatile fraction;

the improvement wherein said gas is cooled sufficiently to partially condense it; and (1) said partially condensed gas is separated thereby to provide a vapor stream and a condensed stream;

(2) said vapor stream is thereafter divided into gaseous first and second streams;

(3) said gaseous first stream is cooled to condense substantially all of it and is thereafter expanded to said lower pressure whereby it is further cooled;

(4) the expanded cooled first stream is then directed in heat exchange relation with a warmer compressed recycle portion of a distillation stream which rises in a fractionation tower; the distillation stream is withdrawn from an upper region of said tower and is thereafter divided into said volatile residue gas fraction and said recycle stream;

(5) said first stream is thereafter supplied at a first mid-column feed position to a distillation column in a lower region of the fractionation tower;

(6) the compressed recycle stream is cooled by said expanded cooled first stream sufficiently to substantially condense it;

(7) the substantially condensed compressed recycle stream is expanded to said lower pressure and supplied to said fractionation tower at a top feed position;

(8) the gaseous second stream is expanded to said lower pressure and supplied to said distillation column at a second mid-column feed position;

(9) at least a portion of said condensed stream is expanded to said lower pressure and is supplied to said distillation column at a third mid-column feed position; and

(10) the pressure of said compressed recycle stream and the quantities and temperatures of said feeds to the column are effective to maintain tower overhead temperature at a temperature whereby the major portion of said $C_2$ components, $C_3$ components and heavier hydrocarbon components is recovered in said relatively less volatile fraction.

8. In a process for the separation of a gas containing methane, $C_2$ components, $C_3$ components and heavier hydrocarbon components into a volatile residue gas fraction containing a major portion of said methane and said $C_2$ components and a relatively less volatile fraction containing a major portion of said $C_3$ components and heavier components, in which process (a) said gas is cooled under pressure to provide a cooled stream;

(b) said cooled stream is expanded to a lower pressure whereby it is further cooled; and (c) said further cooled stream is fractionated at said lower pressure whereby the major portion of said $C_3$ components and heavier hydrocarbon components is recovered in said relatively less volatile fraction;

the improvement wherein said gas is cooled sufficiently to partially condense it; and (1) said partially condensed gas is separated thereby to provide a vapor stream and a condensed stream;

(2) said vapor stream is thereafter divided into gaseous first and second streams;

(3) said gaseous first stream is cooled to condense substantially all of it and is thereafter expanded to said lower pressure whereby it is further cooled;

(4) the expanded cooled first stream is then directed in heat exchange relation with a warmer compressed recycle portion of a distillation stream which rises in a fractionation tower; the distillation stream is withdrawn from an upper region of said tower and is thereafter divided into said volatile residue gas fraction and said recycle stream;

(5) said first stream is thereafter supplied at a first mid-column feed position to a distillation column in a lower region of the fractionation tower;

(6) the compressed recycle stream is cooled by said expanded cooled first stream sufficiently to substantially condense it;

(7) the substantially condensed compressed recycle stream is expanded to said lower pressure and supplied to said fractionation tower at a top feed position;

(8) the gaseous second stream is expanded to said lower pressure and supplied to said distillation column at a second mid-column feed position;

(9) at least a portion of said condensed stream is expanded to said lower pressure and is supplied to said distillation column at a third mid-column feed position; and

(10) the pressure of said compressed recycle stream and the quantities and temperatures of said feeds to the column are effective to maintain tower overhead temperature at a temperature whereby the major portion of said $C_3$ components and heavier hydrocarbon components is recovered in said relatively less volatile fraction.

9. In a preocess for the separation of a gas containing methane, $C_2$ components, $C_3$ components and heavier hydrocarbon components into a volatile residue gas fraction containing a major portion of said methane and a relatively less volatile fraction containing a major portion of said $C_2$ components, $C_3$ components and heavier components, in which process (a) said gas is cooled under pressure to provide a cooled stream;

(b) said cooled stream is expanded to a lower pressure whereby it is further cooled; and (c) said further cooled stream is fractionated at said lower pressure whereby the major portion of said $C_2$ components, $C_3$ components and heavier hydrocarbon components is recovered in said relatively less volatile fraction;

the improvement wherein prior to cooling, said gas is divided into gaseous first and second streams; and (1) said gaseous first stream is cooled to condense substantially all of it and is thereafter expanded to said lower pressure whereby it is further cooled;

(2) the expanded cooled first stream is then directed in heat exchange relation with a warmer compressed recycle portion of a distillation stream which rises in a fractionation tower; the distillation stream is withdrawn from an upper region of said tower and is thereafter divided into said volatile residue gas fraction and said recycle stream;

(3) said first stream is thereafter supplied at a first mid-column feed position to a distillation column in a lower region of the fractionation tower;

(4) said compressed recycle stream is cooled by said expanded cooled first stream sufficiently to substantially condense it;

(5) said substantially condensed compressed recycle stream is expanded to said lower pressure and supplied to said fractionation tower at a top feed position;

(6) said gaseous second stream is cooled under pressure sufficiently to partially condense it;

(7) said partially condensed second stream is separated thereby to provide a vapor stream and a condensed stream;

(8) said vapor stream is expanded to said lower pressure and supplied to said distillation column at a second mid-column feed position;

(9) at least a portion of said condensed stream is expanded to said lower pressure and is supplied to said distillation column at a third mid-column feed position; and

(10) the pressure of said compressed recycle stream and the quantities and temperatures of said feeds to the column are effective to maintain the tower overhead temperature at a temperature whereby the major portion of said $C_2$ components, $C_3$ components and heavier hydrocarbon components is recovered in said relatively less volatile fraction.

10. In a process for the separation of a gas containing methane, $C_2$ components, $C_3$ components and heavier hydrocarbon components into a volatile residue gas fraction containing a major portion of said methane and said $C_2$ components and a relatively less volatile fraction containing a major portion of said $C_3$ components and heavier components, in which process (a) said gas is cooled under pressure to provide a cooled stream;

(b) said cooled stream is expanded to a lower pressure whereby it is further cooled; and (c) said further cooled stream is fractionated at said lower pressure whereby the major portion of said $C_3$ components and heavier hydrocarbon components is recovered in said relatively less volatile fraction;

the improvement wherein prior to cooling, said gas is divided into gaseous first and second streams; and (1) said gaseous first stream is cooled to condense substantially all of it and is thereafter expanded to said lower pressure whereby it is further cooled;

(2) the expanded cooled first stream is then directed in heat exchange relation with a warmer compressed recycle portion of a distillation stream which rises in a fractionation tower; the distillation stream is withdrawn from an upper region of said tower and is thereafter divided into said volatile residue gas fraction and said recycle stream;

(3) said first stream is thereafter supplied at a first mid-column feed position to a distillation column in a lower region of the fractionation tower;

(4) said compressed recycle stream is cooled by said expanded cooled first stream sufficiently to substantially condense it;

(5) said substantially condensed compressed recycle stream is expanded to said lower pressure and supplied to said fractionation tower at a top feed position;

(6) said gaseous second stream is cooled under pressure sufficiently to partially condense it;

(7) said partially condensed second stream is separated thereby to provide a vapor stream and a condensed stream;

(8) said vapor stream is expanded to said lower pressure and supplied to said distillation column at a second mid-column feed position;

(9) at least a portion of said condensed stream is expanded to said lower pressure and is supplied to said distillation column at a third mid-column feed position; and

(10) the pressure of said compressed recycle stream and the quantities and temperatures of said feeds to the column are effective to maintain the tower overhead temperature at a temperature whereby the major portion of said $C_3$ components and heavier hydrocarbon components is recovered in said relatively less volatile fraction.

11. In a process for the separation of a gas containing methane, $C_2$ components, $C_3$ components and heavier hydrocarbon components into a volatile residue gas fraction containing a major portion of said methane and a relatively less volatile fraction containing a major portion of said $C_2$ components, $C_3$ components and heavier components, in which process (a) said gas is cooled under pressure to provide a cooled stream;

(b) said cooled stream is expanded to a lower pressure whereby it is further cooled; and (c) said further cooled stream is fractionated at said lower pressure whereby the major portion of said $C_2$ components, $C_3$ components and heavier hydrocarbon components is recovered in said relatively less volatile fraction;

the improvement wherein following cooling, said cooled stream is divided into first and second streams; and (1) said first stream is cooled to condense substantially all of it and is thereafter expanded to said lower pressure whereby it is further cooled;

(2) said expanded cooled first stream is directed in heat exchange relation with a warmer compressed recycle portion of a distillation stream which rises in a fractionation tower; the distillation stream is withdrawn from an upper region of said tower and is thereafter divided into said volatile residue gas fraction and said recycle stream;

(3) said first stream is thereafter supplied at a first mid-column feed position to a distillation column in a lower region of the fractionation tower;

(4) said compressed recycle stream is cooled by said expanded cooled first stream sufficiently to substantially condense it;

(5) said substantially condensed compressed recycle stream is expanded to said lower pressure and thereafter supplied to said fractionation tower at a top feed position;

(6) said second stream is cooled sufficiently to partially condense it;

(7) said partially condensed second stream is separated thereby to provide a vapor stream and a condensed stream;

(8) said vapor stream is expanded to said lower pressure and supplied to said distillation column at a second mid-column feed position;

(9) at least a portion of said condensed stream is expanded to said lower pressure and is supplied to said distillation column at a third mid-column feed position; and

(10) the pressure of said compressed recycle stream and the quantities and temperatures of said feeds to the column are effective to maintain tower overhead temperature at a temperature whereby the major portion of said $C_2$ components, $C_3$ components and heavier hydrocarbon components is recovered in said relatively less volatile fraction.

12. In a process for the separation of a gas containing methane, $C_2$ components, $C_3$ components and heavier hydrocarbon components into a volatile residue gas fraction containing a major portion of said methane and said $C_2$ components and a relatively less volatile fraction containing a major portion of said $C_3$ components and heavier components, in which process (a) said gas is cooled under pressure to provide a cooled stream;

(b) said cooled stream is expanded to a lower pressure whereby it is further cooled; and (c) said further cooled stream is fractionated at said lower pressure whereby the major portion of said $C_3$ components and heavier hydrocarbon components is recovered in said relatively less volatile fraction;

the improvement wherein following cooling, said cooled stream is divided into first and second streams; and (1) said first stream is cooled to condense substantially all of it and is thereafter expanded to said lower pressure whereby it is further cooled;

(2) said expanded cooled first stream is directed in heat exchange relation with a warmer compressed recycle portion of a distillation stream which rises in a fractionation tower; the distillation stream is withdrawn from an upper region of said tower and is thereafter divided into said volatile residue gas fraction and said recycle stream;

(3) said first stream is thereafter supplied at a first mid-column feed position to a distillation column in a lower region of the fractionation tower;

(4) said compressed recycle stream is cooled by said expanded cooled first stream sufficiently to substantially condense it;

(5) said substantially condensed compressed recycle stream is expanded to said lower pressure and thereafter supplied to said fractionation tower at a top feed position;

(6) said second stream is cooled sufficiently to partially condense it;

(7) said partially condensed second stream is separated thereby to provide a vapor stream and a condensed stream;

(8) said vapor stream is expanded to said lower pressure and supplied to said distillation column at a second mid-column feed position;

(9) at least a portion of said condensed stream is expanded to said lower pressure and is supplied to said distillation column at a third mid-column feed position; and

(10) the pressure of said compressed recycle stream and the quantities and temperatures of said feeds to the column are effective to maintain tower overhead temperature at a temperature whereby the major portion of said $C_3$ components and heavier hydrocarbon components is recovered in said relatively less volatile fraction.

13. In a process for the separation of a gas containing methane, $C_2$ components, $C_3$ components and heavier hydrocarbon components into a volatile residue gas fraction containing a major portion of said methane and a relatively less volatile fraction containing a major portion of said $C_2$ components, $C_3$ components and heavier components, in which process (a) said gas is cooled under pressure to provide a cooled stream;

(b) said cooled stream is expanded to a lower pressure whereby it is further cooled; and (c) said further cooled stream is fractionated at said lower pressure whereby the major portion of said $C_2$ components, $C_3$ components and heavier hydrocarbon components is recovered in said relatively less volatile fraction;

the improvement wherein following cooling, said cooled stream is divided into first and second streams; and (1) said first stream is cooled to condense substantially all of it and is thereafter expanded to said lower pressure whereby it is further cooled;

(2) said expanded cooled first stream is then directed in heat exchange relation with a warmer compressed recycle portion of a distillation stream which rises in a fractionation tower; the distillation stream is withdrawn from an upper region of said tower and is thereafter divided into said volatile residue gas fraction and said recycle stream;

(3) said first stream is thereafter supplied at a first mid-column feed position to a distillation column in a lower region of the fractionation tower;

(4) said compressed recycle stream is cooled by said expanded cooled first stream sufficiently to substantially condense it;

(5) said substantially condensed compressed recycle stream is expanded to said lower pressure and supplied to said fractionation tower at a top feed position;

(6) said second stream is expanded to said lower pressure and is supplied to said distillation column at a second mid-column feed position; and (7) the pressure of said compressed recycle stream and the quantities and temperatures of said feeds to the column are effective to maintain tower overhead temperature at a temperature whereby the major portion of said $C_2$ components, $C_3$ components and heavier hydrocarbon components is recovered in said relatively less volatile fraction.

14. In a process for the separation of a gas containing methane, $C_2$ components, $C_3$ components and heavier hydrocarbon components into a volatile residue gas fraction containing a major portion of said methane and said $C_2$ components and a relatively less volatile fraction containing a major portion of said $C_3$ components and heavier components, in which process
  (a) said gas is cooled under pressure to provide a cooled stream;
  (b) said cooled stream is expanded to a lower pressure whereby it is further cooled; and
  (c) said further cooled stream is fractionated at said lower pressure whereby the major portion of said $C_3$ components and heavier hydrocarbon components is recovered in said relatively less volatile fraction;
  the improvement wherein following cooling, said cooled stream is divided into first and second streams; and
  (1) said first stream is cooled to condense substantially all of it and is thereafter expanded to said lower pressure whereby it is further cooled;
  (2) said expanded cooled first stream is then directed in heat exchange relation with a warmer compressed recycle portion of a distillation stream which rises in a fractionation tower; the distillation stream is withdrawn from an upper region of said tower and is thereafter divided into said volatile residue gas fraction and said recycle stream;
  (3) said first stream is thereafter supplied at a first mid-column feed position to a distillation column in a lower region of the fractionation tower;
  (4) said compressed recycle stream is cooled by said expanded cooled first stream sufficiently to substantially condense it;
  (5) said substantially condensed compressed recycle stream is expanded to said lower pressure and supplied to said fractionation tower at a top feed position;
  (6) said second stream is expanded to said lower pressure and is supplied to said distillation column at a second mid-column feed position; and
  (7) the pressure of said compressed recycle stream and the quantities and temperatures of said feeds to the column are effective to maintain tower overhead temperature at a temperature whereby the major portion of said $C_3$ components and heavier hydrocarbon components is recovered in said relatively less volatile fraction.

15. In a process for the separation of a gas containing methane, $C_2$ components, $C_3$ components and heavier hydrocarbon components into a volatile residue gas fraction containing a major portion of said methane and a relatively less volatile fraction containing a major portion of said $C_2$ components, $C_3$ components and heavier components, in which process
  (a) said gas is cooled under pressure to provide a cooled stream;
  (b) said cooled stream is expanded to a lower pressure whereby it is further cooled; and
  (c) said further cooled stream is fractionated at said lower pressure whereby the major portion of said $C_2$ components, $C_3$ components and heavier hydrocarbon components is recovered in said relatively less volatile fraction;
  the improvement wherein prior to cooling, said gas is divided into gaseous first and second streams; and
  (1) said gaseous first stream is cooled to condense substantially all of it and is thereafter expanded to said lower pressure whereby it is further cooled;
  (2) the expanded cooled first stream is then directed in heat exchange relation with a warmer compressed recycle portion of a distillation stream which rises in a fractionation tower; the distillation stream is withdrawn from an upper region of said tower and is thereafter divided into said volatile residue gas fraction and said recycle stream;
  (3) said first stream is thereafter supplied at a first mid-column feed position to a distillation column in a lower region of the fractionation tower;
  (4) said compressed recycle stream is cooled by said expanded cooled first stream sufficiently to substantially condense it;
  (5) said substantially condensed compressed recycle stream is expanded to said lower pressure and supplied to said fractionation tower at a top feed position;
  (6) said gaseous second stream is cooled under pressure and then expanded to said lower pressure and supplied to said distillation column at a second mid-column feed position; and
  (7) the pressure of said compressed recycle stream and the quantities and temperatures of said feeds to the column are effective to maintain the tower overhead temperature at a temperature whereby the major portion of said $C_2$ components, $C_3$ components and heavier hydrocarbon components is recovered in said relatively less volatile fraction.

16. In a process for the separation of a gas containing methane, $C_2$ components, $C_3$ components and heavier hydrocarbon components into a volatile residue gas fraction containing a major portion of said methane and said $C_2$ components and a relatively less volatile fraction containing a major portion of said $C_3$ components and heavier components, in which process
  (a) said gas is cooled under pressure to provide a cooled stream;
  (b) said cooled stream is expanded to a lower pressure whereby it is further cooled; and
  (c) said further cooled stream is fractionated at said lower pressure whereby the major portion of said $C_3$ components and heavier hydrocarbon components is recovered in said relatively less volatile fraction;
  the improvement wherein prior to cooling, said gas is divided into gaseous first and second streams; and
  (1) said gaseous first stream is cooled to condense substantially all of it and is thereafter expanded to said lower pressure whereby it is further cooled;
  (2) the expanded cooled first stream is then directed in heat exchange relation with a warmer compressed recycle portion of a distillation stream which rises in a fractionation tower; the distillation stream is withdrawn from an upper region of said tower and is thereafter divided into said volatile residue gas fracton and said recycle stream;
  (3) said first stream is thereafter supplied at a first mid-column feed position to a distillation column in a lower region of the fractionation tower;
  (4) said compressed recycle stream is cooled by said expanded cooled first stream sufficiently to substantially condense it;
  (5) said substantially condensed compressed recycle stream is expanded to said lower pressure and supplied to said fractionation tower at a top feed position;

(6) said gaseous second stream is cooled under pressure and then expanded to said lower pressure and supplied to said distillation column at a second mid-column feed position; and (7) the pressure of said compressed recycle stream and the quantities and temperatures of said feeds to the column are effective to maintain the tower overhead temperature at a temperature whereby the major portion of said $C_3$ components and heavier hydrocarbon components is recovered in said relatively less volatile fraction.

17. The improvement according to claim 1, 2, 3, 4, 5, 6, 7, 8, 9, 10, 11, 12, 13, 14, 15 or 16 wherein said recycle stream is heated prior to compression.

18. The improvement according to claim 1, 2, 3, 4, 5, 6, 7, 8, 9, 10, 11, 12, 13, 14, 15 or 16 wherein said distillation stream is heated prior to being divided into said volatile residue gas fraction and said recycle stream.

19. The improvement according to claim 1, 2, 3, 4, 5 or 6 wherein at least a portion of said condensed stream is expanded to said lower pressure and then supplied to said distillation column at a third mid-column feed position.

20. The improvement according to claim 1, 2, 3, 4, 5 or 6 wherein at least a portion of said condensed stream is expanded to said lower pressure, heated and then supplied to said distillation column at a third mid-column feed position.

21. The improvement according to claim 19 wherein said recycle stream is heated prior to compression.

22. The improvement according to claim 20 wherein said recycle stream is heated prior to compression.

23. The improvement according to claim 19 wherein said distillation stream is heated prior to being divided into said volatile residue gas fraction and said recycle stream.

24. The improvement according to claim 20 wherein said distillation stream is heated prior to being divided into said volatile residue gas fraction and said recycle stream.

25. The improvement according to claim 1 or 2 wherein at least portions of two or more of said combined stream, said second stream and said condensed stream are combined to form a second combined stream and said second combined stream is supplied to said column at a mid-column feed position.

26. The improvement according to claim 25 wherein said recycle stream is heated prior to compression.

27. The improvement according to claim 25 wherein said distillation stream is heated prior to being divided into said volatile residue gas fraction and said recycle stream.

28. The improvement according to claim 3, 4, 5 or 6 wherein at least portions of two or more of said combined stream, said vapor stream and said condensed stream are combined to form a second combined stream and said second combined stream is supplied to said column at a mid-column feed position.

29. The improvement according to claim 28 wherein said recycle stream is heated prior to compression.

30. The improvement according to claim 28 wherein said distillation stream is heated prior to being divided into said volatile residue gas fraction and said recycle stream.

31. The improvement according to claim 7 or 8 wherein at least portions of two or more of said first stream, said second stream and said condensed stream are combined to form a combined stream and said combined stream is supplied to said column at a mid-column feed position.

32. The improvement according to claim 31 wherein said recycle stream is heated prior to compression.

33. The improvement according to claim 31 wherein said distillation stream is heated prior to being divided into said volatile residue gas fraction and said recycle stream.

34. The improvement according to claim 9, 10, 11 or 12 wherein at least portions of two or more of said first stream, said vapor stream and said condensed stream are combined to form a combined stream and said combined stream is supplied to said column at a mid-column feed position.

35. The improvement according to claim 34 wherein said recycle stream is heated prior to compression.

36. The improvement according to claim 34 wherein said distillation stream is heated prior to being divided into said volatile residue gas fraction and said recycle stream.

37. The improvement according to claim 13, 14, 15 or 16 wherein at least portions of said first stream and said second stream are combined to form a combined stream and said combined stream is supplied to said column at a mid-column feed position.

38. The improvement according to claim 37 wherein said recycle stream is heated prior to compression.

39. The improvement according to claim 37 wherein said distillation stream is heated prior to being divided into said volatile residue gas fraction and said recycle stream.

40. The improvement according to claim 7, 8, 9, 10, 11 or 12 wherein,
    (a) said condensed stream is cooled prior to said expansion and then divided into first and second liquid portions;
    (b) said first liquid portion is expanded to said lower pressure and supplied to said column at a mid-column feed position; and
    (c) said second liquid portion is expanded to said lower pressure and supplied to said column at a higher mid-column feed position.

41. The improvement according to claim 40 wherein said recycle stream is heated prior to compression.

42. The improvement according to claim 40 wherein said distillation stream is heated prior to being divided into said volatile residue gas fraction and said recycle stream.

43. The improvement according to claim 40 wherein
    (a) at least part of said second liquid portion is combined with said first stream to form a combined stream and said combined stream is directed in heat exchange relation with said compressed recycle stream;
    (b) the remainder of said second liquid portion is expanded to said lower pressure and supplied to said column at another mid-column feed position.

44. The improvement according to claim 43 wherein said recycle stream is heated prior to compression.

45. The improvement according to claim 43 wherein said distillation stream is heated prior to being divided into said volatile residue gas fraction and said recycle stream.

46. The improvement according to claim 40 wherein said first liquid portion is expanded, directed in heat exchange relation with said condensed stream and is then supplied to said column at a mid-column feed position.

47. The improvement according to claim 46 wherein said recycle stream is heated prior to compression.

48. The improvement according to claim 46 wherein said distillation stream is heated prior to being divided into said volatile residue gas fraction and said recycle stream.

49. The improvement according to claim 40 wherein said second liquid portion is expanded to said lower pressure and at least part of said expanded second liquid portion is combined with said expanded cooled first stream to form a combined stream and said combined stream is directed in heat exchange relation with said compressed recycle stream.

50. The improvement according to claim 49 wherein said recycle stream is heated prior to compression.

51. The improvement according to claim 49 wherein said distillation stream is heated prior to being divided into said volatile residue gas fraction and said recycle stream.

52. The improvement according to claim 7, 8, 9, 10, 11 or 12 wherein said expanded condensed stream is heated prior to being supplied to said distillation column.

53. The improvement according to claim 52 wherein said recycle stream is heated prior to compression.

54. The improvement according to claim 52 wherein said distillation stream is heated prior to being divided into said volatile residue gas fraction and said recycle stream.

55. The improvement according to claim 1, 2, 7, 8, 13, 14, 15 or 16 wherein said second stream is heated after expansion to said lower pressure.

56. The improvement according to claim 55 wherein said recycle stream is heated prior to compression.

57. The improvement according to claim 55 wherein said distillation stream is heated prior to being divided into said volatile residue gas fraction and said recycle stream.

58. The improvement according to claim 3, 4, 5, 6, 9, 10, 11 or 12 wherein said vapor stream is heated after expansion to said lower pressure.

59. The improvement according to claim 58 wherein said recycle stream is heated prior to compression.

60. The improvement according to claim 58 wherein said distillation stream is heated prior to being divided into said volatile residue gas fraction and said recycle stream.

61. In a process for the separation of a gas containing methane, $C_2$ components, $C_3$ components and heavier hydrocarbon components into a volatile residue gas fraction containing a major portion of said methane and a relatively less volatile fraction containing a major portion of said $C_2$ components, $C_3$ components and heavier components in which process (a) said gas is cooled under pressure to provide a cooled stream;
(b) said cooled stream is expanded to a lower pressure whereby it is further cooled; and
(c) said further cooled stream is fractionated at said lower pressure whereby the major portion of said $C_2$ components, $C_3$ components and heavier hydrocarbon components is recovered in said relatively less volatile fraction;

the improvement wherein said gas is cooled sufficiently to partially condense it; and (1) said partially condensed gas is separated thereby to provide a vapor stream and a condensed stream;
(2) said vapor stream is thereafter divided into gaseous first and second streams:
(3) said gaseous first stream is cooled to condense substantially all of it and is thereafter expanded to said lower pressure and supplied at a first mid-column feed position to a distillation column in a lower region of a fractionation tower;
(4) said gaseous second stream is expanded to said lower pressure and is then supplied to said distillation column at a second mid-column feed position;
(5) at least a portion of said condensed stream is expanded to said lower pressure and is then supplied to said distillation column at a third mid-column feed position;
(6) a distillation stream is withdrawn from an upper region of said fractionation tower and is thereafter divided into said volatile residue gas fraction and a recycle stream;
(7) a cold liquid stream is withdrawn from said distillation column at a mid-column position;
(8) said recycle stream is compressed and directed in heat exchange relation with said cold liquid stream whereby said compressed recycle stream is cooled by said cold liquid stream sufficiently to substantially condense it and said cold liquid stream is heated and partially vaporized;
(9) the substantially condensed recycle stream is expanded to said lower pressure and supplied to said fractionation tower at a top feed position; and
(10) the pressure of said compressed recycle stream and the quantities and temperature of said feeds to the column are effective to maintain tower overhead temperature at a temperature whereby the major portion of said $C_2$ components, $C_3$ components and heavier components is recovered in said relatively less volatile fraction.

62. In a process for the separation of a gas containing methane, $C_2$ components, $C_3$ components and heavier hydrocarbon components into a volatile residue gas fraction containing a major portion of said methane and said $C_2$ components and a relatively less volatile fraction containing a major portion of said $C_3$ components and heavier components in which process (a) said gas is cooled under pressure to provide a cooled stream;
(b) said cooled stream is expanded to a lower pressure whereby it is further cooled; and
(c) said further cooled stream is fractionated at said lower pressure whereby the major portion of said $C_3$ components and heavier hydrocarbon components is recovered in said relatively less volatile fraction;

the improvement wherein said gas is cooled sufficiently to partially condense it; and (1) said partially condensed gas is separated thereby to provide a vapor stream and a condensed stream;
(2) said vapor stream is thereafter divided into gaseous first and second streams;
(3) said gaseous first stream is cooled to condense substantially all of it and is thereafter expanded to said lower pressure and supplied at a first mid-column feed position to a distillation column in a lower region of a fractionation tower;
(4) said gaseous second stream is expanded to said lower pressure and is then supplied to said distillation column at a second mid-column feed position;

(5) at least a portion of said condensed stream is expanded to said lower pressure and is then supplied to said distillation column at a third mid-column feed position;

(6) a distillation stream is withdrawn from an upper region of said fractionation tower and is thereafter divided into said volatile residue gas fraction and a recycle stream;

(7) a cold liquid stream is withdrawn from said distillation column at a mid-column position;

(8) said recycle stream is compressed and directed in heat exchange relation with said cold liquid stream whereby said compressed recycle stream is cooled by said cold liquid stream sufficiently to substantially condense it and said cold liquid stream is heated and partially vaporized;

(9) the substantially condensed recycle stream is expanded to said lower pressure and supplied to said fractionation tower at a top feed position; and

(10) the pressure of said compressed recycle stream and the quantities and temperature of said feeds to the column are effective to maintain tower overhead temperature at a temperature whereby the major portion of said $C_3$ components and heavier components is recovered in said relatively less volatile fraction.

63. In a process for the separation of a gas containing methane, $C_2$ components, $C_3$ components and heavier hydrocarbon components into a volatile residue gas fraction containing a major portion of said methane and a relatively less volatile fraction containing a major portion of said $C_2$ components, $C_3$ components and heavier components in which process (a) said gas is cooled under pressure to provide a cooled stream;

(b) said cooled stream is expanded to a lower pressure whereby it is further cooled; and (c) said further cooled stream is fractionated at said lower pressure whereby the major portion of said $C_2$ components, $C_3$ components and heavier hydrocarbon components is recovered in said relatively less volatile fraction;

the improvement wherein said gas is cooled sufficiently to partially condense it; and (1) said partially condensed gas is separated thereby to provide a vapor stream and a condensed stream;

(2) said vapor stream is thereafter divided into gaseous first and second streams;

(3) at least a portion of said condensed stream is combined with said gaseous first stream to form a combined stream and said combined stream is cooled to condense substantially all of it and is thereafter expanded to said lower pressure and supplied at a first mid-column feed position to a distillation column in a lower region of a fractionation tower;

(4) said gaseous second stream is expanded to said lower pressure and is then supplied to said distillation column at a second mid-column feed position;

(5) a distillation stream is withdrawn from an upper region of said fractionation tower and is thereafter divided into said volatile residue gas fraction and a recycle stream;

(6) a cold liquid stream is withdrawn from said distillation column at a mid-column position;

(7) said recycle stream is compressed and directed in heat exchange relation with said cold liquid stream whereby said compressed recycle stream is cooled by said cold liquid stream sufficiently to substantially condense it and said cold liquid stream is heated and partially vaporized;

(8) the substantially condensed recycle stream is expanded to said lower pressure and supplied to said fractionation tower at a top feed position; and (9) the pressure of said compressed recycle stream and the quantities and temperature of said feeds to the column are effective to maintain tower overhead temperature at a temperature whereby the major portion of said $C_2$ components, $C_3$ components and heavier components is recovered in said relatively less volatile fraction.

64. In a process for the separation of a gas containing methane, $C_2$ components, $C_3$ components and heavier hydrocarbon components into a volatile residue gas fraction containing a major portion of said methane and said $C_2$ components and a relatively less volatile fraction containing a major portion of said $C_3$ components and heavier components in which process (a) said gas is cooled under pressure to provide a cooled stream;

(b) said cooled stream is expanded to a lower pressure whereby it is further cooled; and (c) said further cooled stream is fractionated at said lower pressure whereby the major portion of said $C_3$ components and heavier hydrocarbon components is recovered in said relatively less volatile fraction;

the improvement wherein said gas is cooled sufficiently to partially condense it; and (1) said partially condensed gas is separated thereby to provide a vapor stream and a condensed stream;

(2) said vapor stream is thereafter divided into gaseous first and second streams;

(3) at least a portion of said condensed stream is combined with said gaseous first stream to form a combined stream and said combined stream is cooled to condense substantially all of it and is thereafter expanded to said lower pressure and supplied at a first mid-column feed position to a distillation column in a lower region of a fractionation tower;

(4) said gaseous second stream is expanded to said lower pressure and is then supplied to said distillation column at a second mid-column feed position;

(5) a distillation stream is withdrawn from an upper region of said fractionation tower and is thereafter divided into said volatile residue gas fraction and a recycle stream;

(6) a cold liquid stream is withdrawn from said distillation column at a mid-column position;

(7) said recycle stream is compressed and directed in heat exchange relation with said cold liquid stream whereby said compressed recycle stream is cooled by said cold liquid stream sufficiently to substantially condense it and said cold liquid stream is heated and partially vaporized;

(8) the substantially condensed recycle stream is expanded to said lower pressure and supplied to said fractionation tower at a top feed position; and (9) the pressure of said compressed recycle stream and the quantities and temperature of said feeds to the column are effective to maintain tower overhead temperature at a temperature whereby the major portion of said $C_3$ components and heavier components is recovered in said relatively less volatile fraction.

65. The improvement according to claim 61, 62, 63 or 64 wherein said recycle stream is heated prior to compression.

66. The improvement according to claim 61, 62, 63 or 64 wherein said distillation stream is heated prior to being divided into said volatile residue gas fraction and said recycle stream.

67. In an apparatus for the separation of a gas containing methane, $C_2$ components, $C_3$ components and heavier hydrocarbon components into a volatile residue gas fraction containing a major portion of said methane and a relatively less volatile fraction containing a major portion of said $C_2$ components, $C_3$ components and heavier components, in said apparatus there being
   (a) a first cooling means to cool said gas under pressure connected to provide a cooled stream under pressure;
   (b) a first expansion means connected to receive at least a portion of said cooled stream under pressure and to expand it to a lower pressure, whereby said stream is further cooled; and
   (c) a fractionation tower connected to said first expansion means to receive the further cooled stream therefrom;
the improvement wherein said apparatus includes
   (1) first cooling means adapted to cool said feed gas under pressure sufficiently to partially condense it;
   (2) separation means connected to said first cooling means to receive said partially condensed feed and to separate it into a vapor and a condensed stream;
   (3) first dividing means connected to said separation means to receive said vapor and to divide said vapor into first and second streams;
   (4) combining means connected to combine said condensed stream and said first stream into a combined stream;
   (5) second cooling means connected to said combining means to receive said combined stream and to cool it sufficiently to substantially condense it;
   (6) second expansion means connected to said second cooling means to receive said substantially condensed combined stream and to expand it to said lower pressure;
   (7) heat exchange means connected to said second expansion means to receive said expanded combined stream and to heat it, said heat exchange means further connected to compressing means to receive a compressed recycle portion of a distillation stream which rises in the fractionation tower, wherein said heat exchange means cools and substantially condenses said compressed recycle stream; said heat exchange means being further connected to a distillation column in a lower region of the fractionation tower to supply said expanded combined stream to said distillation column at a first mid-column feed position; said heat exchange means being further connected to a third expansion means;
   (8) said third expansion means being connected to said heat exchange means to receive said substantially condensed compressed recycle stream and expand it to said lower pressure, said third expansion means being further connected to said fractionation tower to supply said expanded condensed recycle stream to the tower at a top feed position;
   (9) second dividing means connected to said fractionation tower to receive said distillation stream and to divide it into said volatile residue gas fraction and said recycle stream;
   (10) compressing means connected to said dividing means to receive said recycle stream and to compress it, said compressing means being further connected to said heat exchange means;
   (11) said first expansion means being connected to said dividing means to receive said second stream and to expand it to said lower pressure, said first expansion means being further connected to said distillation column to supply said expanded second stream to said column at a second mid-column feed position; and
   (12) control means adapted to regulate the pressure of said compressed recycle stream and the quantities and temperatures of said combined stream, said second stream and said recycle stream to maintain column overhead temperature at a temperature whereby the major portion of said $C_2$ components, $C_3$ components and heavier components is recovered in said relatively less volatile fraction.

68. In an apparatus for the separation of a gas containing methane, $C_2$ components, $C_3$ components and heavier hydrocarbon components into a volatile residue gas fraction containing a major portion of said methane and said $C_2$ components and a relatively less volatile fraction containing a major portion of said $C_3$ components and heavier components, in said apparatus there being
   (a) a first cooling means to cool said gas under pressure connected to provide a cooled stream under pressure;
   (b) a first expansion means connected to receive at least a portion of said cooled stream under pressure and to expand it to a lower pressure, whereby said stream is further cooled; and
   (c) a fractionation tower connected to said first expansion means to receive the further cooled stream therefrom;
the improvement wherein said apparatus includes
   (1) first cooling means adapted to cool said feed gas under pressure sufficiently to partially condense it;
   (2) separation means connected to said first cooling means to receive said partially condensed feed and to separate it into a vapor and a condensed stream;
   (3) first dividing means connected to said separation means to receive said vapor and to divide said vapor into first and second streams;
   (4) combining means connected to combine said condensed stream and said first stream into a combined stream;
   (5) second cooling means connected to said combining means to receive said combined stream and to cool it sufficiently to substantially condense it;
   (6) second expansion means connected to said second cooling means to receive said substantially condensed combined stream and to expand it to said lower pressure;
   (7) heat exchange means connected to said second expansion means to receive said expanded combined stream and to heat it, said heat exchange means further connected to compressing means to receive a compressed recycle portion of a distillation stream which rises in the fractionation tower, wherein said heat exchange means cools and substantially condenses said compressed recycle stream; said heat exchange means having further connected to a distillation column in a lower region of the fractionation tower to supply said expanded combined stream to said distillation column at a first mid-column feed position; said heat exchange means being further connected to a third expansion means;

(8) said third expansion means being connected to said heat exchange means to receive said substantially condensed compressed recycle stream and expand it to said lower pressure, said third expansion means being further connected to said fractionation tower to supply said expanded condensed recycle stream to the tower at a top feed position;

(9) second dividing means connected to said fractionation tower to receive said distillation stream and to divide it into said volatile residue gas fraction and said recycle stream;

(10) compressing means connected to said dividing means to receive said recycle stream and to compress it, said compressing means being further connected to said heat exchange means;

(11) said first expansion means being connected to said dividing means to receive said second stream and to expand it to said lower pressure, said first expansion means being further connected to said distillation column to supply said expanded second stream to said column at a second mid-column feed position; and

(12) control means adapted to regulate the pressure of said compressed recycle stream and the quantities and temperatures of said combined stream, said second stream and said recycle stream to maintain column overhead temperature at a temperature whereby the major portion of said $C_3$ components and heavier components is recovered in said relatively less volatile fraction.

69. In an apparatus for the separation of a gas containing methane, $C_2$ components, $C_3$ components and heavier hydrocarbon components into a volatile residue gas fraction containing a major portion of said methane and a relatively less volatile fraction containing a major portion of said $C_2$ components, $C_3$ components and heavier components; in said apparatus there being (a) a first cooling means to cool said gas under pressure connected to provide a cooled stream under pressure;

(b) a first expansion means connected to receive at least a portion of said cooled stream under pressure and to expand it to a lower pressure, whereby said stream is further cooled; and (c) a fractionation tower connected to said expansion means to receive the further cooled stream therefrom;

the improvement wherein said apparatus includes (1) first dividing means prior to said first cooling means to divide said feed gas into a first gaseous stream and a second gaseous stream;

(2) second cooling means connected to said dividing means to receive said first stream and to cool it sufficiently to substantially condense it;

(3) second expansion means connected to said second cooling means to receive the substantially condensed first stream therefrom and to expand it to said lower pressure;

(4) heat exchange means connected to said second expansion means to receive said expanded first stream and to heat it, said heat exchange means being further connected to compressing means to receive a compressed recycle portion of a distillation stream which rises in the fractionation tower, wherein said heat exchange means cools and substantially condenses said compressed recycle stream; said heat exchange means being further connected to a distillation column in a lower region of the fractionation tower to supply said heated first stream to the column at a first mid-column feed position; said heat exchange means being further connected to a third expansion means;

(5) said third expansion means being connected to said heat exchange means to receive said substantially condensed recycle stream and to expand it to said lower pressure, said third expansion means being further connected to said fractionation tower to supply said expanded condensed recycle stream to the tower at a top feed position;

(6) second dividing means connected to said fractionation tower to receive said distillation stream and to divide it into said volatile residue gas fraction and said recycle stream;

(7) compressing means connected to said dividing means to receive said recycle stream and to compress it, said compressing means being further connected to said heat exchange means;

(8) said first cooling means being connected to said first dividing means to receive said second stream and to cool it;

(9) said first expansion means being connected to said first cooling means to receive said cooled second stream and to expand and further cool it; said first expansion means being further connected to said distillation column to supply said second stream to the column at a second mid-column feed position; and

(10) control means adapted to regulate the pressure of said compressed recycle stream and the quantities and temperatures of said first stream, said second stream and said recycle stream to maintain column overhead temperature at a temperature whereby the major portion of said $C_2$ components, $C_3$ components and heavier components is recovered in said relatively less volatile fraction.

70. In an apparatus for the separation of a gas containing methane, $C_2$ components, $C_3$ components and heavier hydrocarbon components into a volatile residue gas fraction containing a major portion of said methane and said $C_2$ components and a relatively less volatile fraction containing a major portion of said $C_3$ components and heavier components; in said apparatus there being (a) a first cooling means to cool said gas under pressure connected to provide a cooled stream under pressure;

(b) a first expansion means connected to receive at least a portion of said cooled stream under pressure and to expand it to a lower pressure, whereby said stream is further cooled; and (c) a fractionation tower connected to said expansion means to receive the further cooled stream therefrom;

the improvement wherein said apparatus includes (1) first dividing means prior to said first cooling means to divide said feed gas into a first gaseous stream and a second gaseous stream;

(2) second cooling means connected to said dividing means to receive said first stream and to cool it sufficiently to substantially condense it;

(3) second expansion means connected to said second cooling means to receive the substantially condensed first stream therefrom and to expand it to said lower pressure;

(4) heat exchange means connected to said second expansion means to receive said expanded first stream and to heat it, said heat exchange means being further connected to compressing means to receive a compressed recycle portion of a distillation stream which rises in the fractionation tower, wherein said heat exchange means cools and substantially condenses said compressed recycle stream; said heat exchange means being further connected to a distillation column in a lower region of the fractionation tower to supply said heated first stream to the column at a first mid-column feed position; said heat exchange means being further connected to a third expansion means;

(5) said third expansion means being connected to said heat exchange means to receive said substantially condensed recycle stream and to expand it to said lower pressure, said third expansion means being further connected to said fractionation tower to supply said expanded condensed recycle stream to the tower at a top feed position;

(6) second dividing means connected to said fractionation tower to receive said distillation stream and to divide it into said volatile residue gas fraction and said recycle stream;

(7) compressing means connected to said dividing means to receive said recycle stream and to compress it, said compressing means being further connected to said heat exchange means;

(8) said first cooling means being connected to said first dividing means to receive said second stream and to cool it;

(9) said first expansion means being connected to said first cooling means to receive said cooled second stream and to expand and further cool it; said first expansion means being further connected to said distillation column to supply said second stream to the column at a second mid-column feed position; and

(10) control means adapted to regulate the pressure of said compressed recycle stream and the quantities and temperatures of said first stream, said second stream and said recycle stream to maintain column overhead temperature at a temperature whereby the major portion of said $C_3$ components and heavier components is recovered in said relatively less volatile fraction.

71. In an apparatus for the separation of a gas containing methane, $C_2$ components, $C_3$ components and heavier hydrocarbon components into a volatile residue gas fraction containing a major portion of said methane and a relatively less volatile fraction containing a major portion of said $C_2$ components, $C_3$ components and heavier components; in said apparatus there being (a) a first cooling means to cool said gas under pressure connected to provide a cooled stream under pressure;

(b) a first expansion means connected to receive at least a portion of said cooled stream under pressure and to expand it to a lower pressure, whereby said stream is further cooled; and (c) a fractionation tower connected to said first expansion means to receive the further cooled stream therefrom;

the improvement wherein said apparatus includes (1) first dividing means after said first cooling means to divide said cooled stream into a first stream and a second stream.

(2) second cooling means connected to said first dividing means to receive said first stream and to cool it sufficiently to substantially condense it;

(3) second expansion means connected to said second cooling means to receive the substantially condensed first stream therefrom and to expand it to said lower pressure;

(4) heat exchange means connected to said second expansion means to receive said expanded first stream and to heat it, said heat exchange means being further connected to compressing means to receive a compressed recycle portion of a distillation stream which rises in the fractionation tower, wherein said heat exchange means cools and substantially condenses said compressed recycle stream; said heat exchange means being further connected to a distillation column in a lower region of the fractionation tower to supply said heated expanded first stream to said distillation column at a first mid-column feed position; said heat exchange means being further connected to a third expansion means;

(5) said third expansion means connected to said heat exchange means to receive said substantially condensed recycle stream therefrom and expand it to said lower pressure, said third expansion means being further connected to said fractionation tower to supply said expanded recycle stream to said tower at a top feed position;

(6) second dividing means connected to said fractionation tower to receive said distillation stream and to divide into said volatile residue gas fraction and said recycle stream;

(7) compressing means connected to said second dividing means to receive said recycle stream and compress it, said compressing means being further connected to said heat exchange means;

(8) said first expansion means being connected to said first dividing means to receive said second stream and to expand and cool it; said first expansion means being further connected to said distillation column to supply said second stream to the column at a second mid-column feed position; and (9) control means adapted to regulate the pressure of said compressed recycle stream and the quantities and temperatures of said first stream, said second stream and said recycle stream to maintain column overhead temperature at a temperature whereby the major portion of said $C_2$ components, $C_3$ components and heavier components is recovered in said relatively less volatile fraction.

72. In an apparatus for the separation of a gas containing methane, $C_2$ components, $C_3$ components and heavier hydrocarbon components into a volatile residue gas fraction containing a major portion of said methane and said $C_2$ components and a relatively less volatile fraction containing a major portion of said $C_3$ components and heavier components; in said apparatus there being (a) a first cooling means to cool said gas under pressure connected to provide a cooled stream under pressure;

(b) a first expansion means connected to receive at least a portion of said cooled stream under pressure and to expand it to a lower pressure, whereby said stream is further cooled; and (c) a fractionation tower connected to said first expansion means to receive the further cooled stream therefrom;

the improvement wherein said apparatus includes (1) first dividing means after said first cooling means to divide said cooled stream into a first stream and a second stream;

(2) second cooling means connected to said first dividing means to receive said first stream and to cool it sufficiently to substantially condense it;

(3) second expansion means connected to said second cooling means to receive the substantially condensed first stream therefrom and to expand it to said lower pressure;

(4) heat exchange means connected to said second expansion means to receive said expanded first stream and to heat it, said heat exchange means being further connected to compressing means to receive a compressed recycle portion of a distillation stream which rises in the fractionation tower, wherein said heat exchange means cools and substantially condenses said compressed recycle stream; said heat exchange means being further connected to a distillation column in a lower region of the fractionation tower to supply said heated expanded first stream to said distillation column at a first mid-column feed position; said heat exchange means being further connected to a third expansion means;

(5) said third expansion means connected to said heat exchange means to receive said substantially condensed recycle stream therefrom and expand it to said lower pressure, said third expansion means being further connected to said fractionation tower to supply said expanded recycle stream to said tower at a top feed position;

(6) second dividing means connected to said fractionation tower to receive said distillation stream and to divide into said volatile residue gas fraction and said recycle stream;

(7) compressing means connected to said second dividing means to receive said recycle stream and compress it, said compressing means being further connected to said heat exchange means;

(8) said first expansion means being connected to said first dividing means to receive said second stream and to expand and cool it; said first expansion means being further connected to said distillation column to supply said second stream to the column at a second mid-column feed position; and (9) control means adapted to regulate the pressure of said compressed recycle stream and the quantities and temperatures of said first stream, said second stream and said recycle stream to maintain column overhead temperature at a temperature whereby the major portion of said $C_3$ components and heavier components is recovered in said relatively less volatile fraction.

* * * * *

UNITED STATES PATENT AND TRADEMARK OFFICE
CERTIFICATE OF CORRECTION

PATENT NO. : 4,889,545

DATED : 12/26/89

INVENTOR(S) : ROY E. CAMPBELL ET AL.

It is certified that error appears in the above-identified patent and that said Letters Patent is hereby corrected as shown below:

Col. 6, line 45, "exchanger 10" should read --exchanger 12--;

Col. 7, line 31, "demethanize" should read --demethanizer--;

Col. 10, line 35, "show" should read --shows--;

Col. 13, line 38, "form" should read --from--;

Col. 15, line 36, after "must" insert --also--;

Col. 22, line 60, "preocess" should read --process--;

Col. 40, line 36, "divide" should read --divide it--.

Signed and Sealed this

Fifth Day of March, 1991

Attest:

HARRY F. MANBECK, JR.

*Attesting Officer*  *Commissioner of Patents and Trademarks*

UNITED STATES PATENT AND TRADEMARK OFFICE
CERTIFICATE OF CORRECTION

PATENT NO. : 4,889,545

DATED : December 26, 1989

INVENTOR(S) : Roy E. Campbell et al.

It is certified that error appears in the above-identified patent and that said Letters Patent is hereby corrected as shown below:

Col. 16, line 32, "reaction" should read --fraction--.

Signed and Sealed this

Eleventh Day of August, 1992

Attest:

DOUGLAS B. COMER

Attesting Officer

Acting Commissioner of Patents and Trademarks